United States Patent
Honjo et al.

(10) Patent No.: US 7,794,975 B2
(45) Date of Patent: Sep. 14, 2010

(54) POLYPEPTIDE ESDN, POLYNUCLEOTIDES ENCODING THE POLYPEPTIDE, AND UTILITY OF THE POLYPEPTIDE

(75) Inventors: Tasuku Honjo, Kyoto (JP); Kei Tashiro, Kyoto (JP); Kazuhiro Kobuke, Kyoto (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 579 days.

(21) Appl. No.: 11/688,170

(22) Filed: Mar. 19, 2007

(65) Prior Publication Data

US 2007/0172892 A1 Jul. 26, 2007

Related U.S. Application Data

(62) Division of application No. 11/055,679, filed on Feb. 11, 2005, now Pat. No. 7,217,786, which is a division of application No. 10/191,436, filed on Jul. 10, 2002, now Pat. No. 6,900,031.

(30) Foreign Application Priority Data

Dec. 27, 2001 (JP) .............................. 2001-397725

(51) Int. Cl.
*C12P 21/06* (2006.01)
*A61K 38/00* (2006.01)
*A61K 51/00* (2006.01)

(52) U.S. Cl. ..................... 435/69.1; 514/2; 530/324; 424/1.69

(58) Field of Classification Search ..................... None
See application file for complete search history.

(56) References Cited

U.S. PATENT DOCUMENTS

| 5,536,637 A | 7/1996 | Jacobs |
| 6,900,031 B2 * | 5/2005 | Honjo et al. ............... 435/69.1 |
| 2003/0032154 A1 | 2/2003 | Gu et al. |

FOREIGN PATENT DOCUMENTS

WO 00/12532 A1 3/2000

OTHER PUBLICATIONS

Kobuke et al., ESDN, a novel neuropilin-like membrane protein cloned from vascular cells with the longest secretory signal sequence among eukaryotes, is up-regulated after vascular injury. J. Biol. Chem. (Sep. 7, 2001) 276:34105-34114.
Sequence report, TrEMBLrel. 19, created Dec. 1, 2001. Result 1.
Manning et al. Stability of Protein Pharmaceuticles. Pharmaceutical Research (1989) 6:903-918.
Benet et al. Pharmacokenitics: The dynamics of Drug Absorption, Distribution, and Elimination. McGraw-Hill (1990) 3-32.

* cited by examiner

*Primary Examiner*—Maury Audet
(74) *Attorney, Agent, or Firm*—Sughrue Mion, PLLC

(57) ABSTRACT

The invention discloses a useful and novel factor (polypeptide) which plays an important role for morbid vascular smooth muscle in restenosis after percutaneous transluminal coronany angioplasty (PTCA) and arterial sclerosis in the field of cardiovascular system.

5 Claims, 7 Drawing Sheets human mouse hESDN-FL hESDN-ΔEC hESDN-ΔCy mESDN-Ex(Edns)

mESDN-Ex(CD5)

▦ endogenous signal sequence
▧ CD5 signal sequence
▥ extracellular domain
■ transmembrane domain
▦ cytoplasmic domain
▤ FLAG tag
■ 6xHis tag anti-FLAG    anti-CUB    anti-FV/VIII anti-CUB anti-FV/VIII anti-ESDN    anti-FLAG    merged

SEQUENCE LISTING

```
<160> NUMBER OF SEQ ID NOS: 24

<210> SEQ ID NO 1
<211> LENGTH: 2328
<212> TYPE: DNA
<213> ORGANISM: Homo sapiens
<220> FEATURE:
<221> NAME/KEY: sig_peptide
<222> LOCATION: (1)..(198)
<220> FEATURE:
<221> NAME/KEY: mat_peptide
<222> LOCATION: (199)..(2328)
<220> FEATURE:
<221> NAME/KEY: CDS
<222> LOCATION: (1)..(2328)
```

<400> SEQUENCE: 1

```
atg gcg agc cgg gcg gtg gtg aga gcc agg cgc tgc ccg cag tgt ccc      48
Met Ala Ser Arg Ala Val Val Arg Ala Arg Arg Cys Pro Gln Cys Pro
-65                 -60                 -55 caa gtc cgg gcc gcg gcc gcc gcc ccc gcc tgg gcc gcg ctc ccc ctc      96
Gln Val Arg Ala Ala Ala Ala Ala Pro Ala Trp Ala Ala Leu Pro Leu
-50                 -45                 -40                 -35 tcc cgc tcc ctc cct ccc tgc tcc aac tcc tcc tcc ttc tcc atg cct     144
Ser Arg Ser Leu Pro Pro Cys Ser Asn Ser Ser Ser Phe Ser Met Pro
                -30                 -25                 -20 ctg ttc ctc ctg ctc tta ctt gtc ctg ctc ctg ctc gag gac gct         192
Leu Phe Leu Leu Leu Leu Leu Val Leu Leu Leu Leu Glu Asp Ala
            -15                 -10                  -5 gga gcc cag caa ggt gat gga tgt gga cac act gta cta ggc cct gag     240
Gly Ala Gln Gln Gly Asp Gly Cys Gly His Thr Val Leu Gly Pro Glu
    -1   1               5                  10 agt gga acc ctt aca tcc ata aac tac cca cag acc tat ccc aac agc     288
Ser Gly Thr Leu Thr Ser Ile Asn Tyr Pro Gln Thr Tyr Pro Asn Ser
 15                  20                  25                  30 act gtt tgt gaa tgg gag atc cgt gta aag atg gga gag aga gtt cgc     336
Thr Val Cys Glu Trp Glu Ile Arg Val Lys Met Gly Glu Arg Val Arg
                 35                  40                  45 atc aaa ttt ggt gac ttt gac att gaa gat tct gat tct tgt cac ttt     384
Ile Lys Phe Gly Asp Phe Asp Ile Glu Asp Ser Asp Ser Cys His Phe
             50                  55                  60 aat tac ttg aga att tat aat gga att gga gtc agc aga act gaa ata     432
Asn Tyr Leu Arg Ile Tyr Asn Gly Ile Gly Val Ser Arg Thr Glu Ile
         65                  70                  75 ggc aaa tac tgt ggt ctg ggg ttg caa atg aac cat tca att gaa tca     480
Gly Lys Tyr Cys Gly Leu Gly Leu Gln Met Asn His Ser Ile Glu Ser
 80                  85                  90 aaa ggc aat gaa atc aca ttg ctg ttc atg agt gga atc cat gtt tct     528
Lys Gly Asn Glu Ile Thr Leu Leu Phe Met Ser Gly Ile His Val Ser
 95                 100                 105                 110 gga cgc gga ttt ttg gcc tca tac tct gtt ata gat aaa caa gat cta     576
Gly Arg Gly Phe Leu Ala Ser Tyr Ser Val Ile Asp Lys Gln Asp Leu
                115                 120                 125 att act tgt ttg gac act gca tcc aat ttt ttg gaa cct gag ttc agt     624
Ile Thr Cys Leu Asp Thr Ala Ser Asn Phe Leu Glu Pro Glu Phe Ser
            130                 135                 140 aag tac tgc cca gct ggt tgt ctg ctt cct ttt gct gag ata tct gga     672
Lys Tyr Cys Pro Ala Gly Cys Leu Leu Pro Phe Ala Glu Ile Ser Gly
        145                 150                 155 aca att cct cat gga tat aga gat tcc tcg cca ttg tgc atg gct ggt     720
Thr Ile Pro His Gly Tyr Arg Asp Ser Ser Pro Leu Cys Met Ala Gly
    160                 165                 170 gtg cat gca gga gta gtg tca aac acg ttg ggc ggc caa atc agt gtt     768
Val His Ala Gly Val Val Ser Asn Thr Leu Gly Gly Gln Ile Ser Val
175                 180                 185                 190 gta att agt aaa ggt att ccc tat tat gaa agt tct ttg gct aac aac     816
Val Ile Ser Lys Gly Ile Pro Tyr Tyr Glu Ser Ser Leu Ala Asn Asn
                195                 200                 205 gtc aca tct gtg gtg gga cac tta tct aca agt ctt ttt aca ttt aag     864
Val Thr Ser Val Val Gly His Leu Ser Thr Ser Leu Phe Thr Phe Lys
            210                 215                 220 aca agt gga tgt tat gga aca ctg ggg atg gag tct ggt gtg atc gcg     912
Thr Ser Gly Cys Tyr Gly Thr Leu Gly Met Glu Ser Gly Val Ile Ala
        225                 230                 235
```

-continued

| | | |
|---|---|---|
| gat cct caa ata aca gca tca tct gtg ctg gag tgg act gac cac aca<br>Asp Pro Gln Ile Thr Ala Ser Ser Val Leu Glu Trp Thr Asp His Thr<br>240                        245                        250 | 960 |
| ggg caa gag aac agt tgg aaa ccc aaa aaa gcc agg ctg aaa aaa cct<br>Gly Gln Glu Asn Ser Trp Lys Pro Lys Lys Ala Arg Leu Lys Lys Pro<br>255                        260                  265                270 | 1008 |
| gga ccg cct tgg gct gct ttt gcc act gat gaa tac cag tgg tta caa<br>Gly Pro Pro Trp Ala Ala Phe Ala Thr Asp Glu Tyr Gln Trp Leu Gln<br>                        275                        280                        285 | 1056 |
| ata gat ttg aat aag gaa aag aaa ata aca ggc att ata acc act gga<br>Ile Asp Leu Asn Lys Glu Lys Lys Ile Thr Gly Ile Ile Thr Thr Gly<br>          290                        295                        300 | 1104 |
| tcc acc atg gtg gag cac aat tac tat gtg tct gcc tac aga atc ctg<br>Ser Thr Met Val Glu His Asn Tyr Tyr Val Ser Ala Tyr Arg Ile Leu<br>               305                        310                        315 | 1152 |
| tac agt gat gat ggg cag aaa tgg act gtg tac aga gag cct ggt gtg<br>Tyr Ser Asp Asp Gly Gln Lys Trp Thr Val Tyr Arg Glu Pro Gly Val<br>320                        325                        330 | 1200 |
| gag caa gat aag ata ttt caa gga aac aaa gat tat cac cag gat gtg<br>Glu Gln Asp Lys Ile Phe Gln Gly Asn Lys Asp Tyr His Gln Asp Val<br>335                        340                  345                350 | 1248 |
| cgt aat aac ttt ttg cca cca att att gca cgt ttt att aga gtg aat<br>Arg Asn Asn Phe Leu Pro Pro Ile Ile Ala Arg Phe Ile Arg Val Asn<br>               355                        360                        365 | 1296 |
| cct acc caa tgg cag cag aaa att gcc atg aaa atg gag ctg ctc gga<br>Pro Thr Gln Trp Gln Gln Lys Ile Ala Met Lys Met Glu Leu Leu Gly<br>                        370                        375                380 | 1344 |
| tgt cag ttt att cct aaa ggt cgt cct cca aaa ctt act caa cct cca<br>Cys Gln Phe Ile Pro Lys Gly Arg Pro Pro Lys Leu Thr Gln Pro Pro<br>         385                        390                        395 | 1392 |
| cct cct cgg aac agc aat gac ctc aaa aac act aca gcc cct cca aaa<br>Pro Pro Arg Asn Ser Asn Asp Leu Lys Asn Thr Thr Ala Pro Pro Lys<br>400                        405                  410 | 1440 |
| ata gcc aaa ggt cgt gcc cca aaa ttt acg caa cca cta caa cct cgc<br>Ile Ala Lys Gly Arg Ala Pro Lys Phe Thr Gln Pro Leu Gln Pro Arg<br>415                        420                  425                430 | 1488 |
| agt agc aat gaa ttt cct gca cag aca gaa caa aca act gcc agt cct<br>Ser Ser Asn Glu Phe Pro Ala Gln Thr Glu Gln Thr Thr Ala Ser Pro<br>               435                        440                        445 | 1536 |
| gat atc aga aat act acc gta act cca aat gta acc aaa gat gta gcg<br>Asp Ile Arg Asn Thr Thr Val Thr Pro Asn Val Thr Lys Asp Val Ala<br>                        450                        455                460 | 1584 |
| ctg gct gca gtt ctt gtc cct gtg ctg gtc atg gtc ctc act act ctc<br>Leu Ala Ala Val Leu Val Pro Val Leu Val Met Val Leu Thr Thr Leu<br>               465                        470                        475 | 1632 |
| att ctc ata tta gtg tgt gct tgg cac tgg aga aac aga aag aaa aaa<br>Ile Leu Ile Leu Val Cys Ala Trp His Trp Arg Asn Arg Lys Lys Lys<br>         480                        485                        490 | 1680 |
| act gaa ggc acc tat gac tta cct tac tgg gac cgg gca ggt tgg tgg<br>Thr Glu Gly Thr Tyr Asp Leu Pro Tyr Trp Asp Arg Ala Gly Trp Trp<br>495                        500                        505                510 | 1728 |
| aaa gga atg aag cag ttt ctt cct gca aaa gca gtg gac cat gag gaa<br>Lys Gly Met Lys Gln Phe Leu Pro Ala Lys Ala Val Asp His Glu Glu<br>                        515                        520                525 | 1776 |
| acc cca gtt cgc tat agc agc agc gaa gtt aat cac ctg agt cca aga<br>Thr Pro Val Arg Tyr Ser Ser Ser Glu Val Asn His Leu Ser Pro Arg<br>                        530                        535                540 | 1824 |
| gaa gtc acc aca gtg ctg cag gct gac tct gca gag tat gct cag cca<br>Glu Val Thr Thr Val Leu Gln Ala Asp Ser Ala Glu Tyr Ala Gln Pro<br>         545                        550                        555 | 1872 |

```
ctg gta gga gga att gtt ggt aca ctt cat caa aga tct acc ttt aaa     1920
Leu Val Gly Gly Ile Val Gly Thr Leu His Gln Arg Ser Thr Phe Lys
    560             565             570 cca gaa gaa gga aaa gaa gca ggc tat gca gac cta gat cct tac aac     1968
Pro Glu Glu Gly Lys Glu Ala Gly Tyr Ala Asp Leu Asp Pro Tyr Asn
575             580             585             590 tca cca ggg cag gaa gtt tat cat gcc tat gct gaa cca ctc cca att     2016
Ser Pro Gly Gln Glu Val Tyr His Ala Tyr Ala Glu Pro Leu Pro Ile
        595             600             605 acg ggg cct gag tat gca acc cca atc atc atg gac atg tca ggg cac     2064
Thr Gly Pro Glu Tyr Ala Thr Pro Ile Ile Met Asp Met Ser Gly His
    610             615             620 ccc aca act tca gtt ggt cag ccc tcc aca tcc act ttc aag gct acg     2112
Pro Thr Thr Ser Val Gly Gln Pro Ser Thr Ser Thr Phe Lys Ala Thr
        625             630             635 ggg aac caa cct ccc cca cta gtg gga act tac aat aca ctt ctc tcc     2160
Gly Asn Gln Pro Pro Pro Leu Val Gly Thr Tyr Asn Thr Leu Leu Ser
640             645             650 agg act gac agc tgc tcc tca gcc cag gcc cag tat gat acc ccg aaa     2208
Arg Thr Asp Ser Cys Ser Ser Ala Gln Ala Gln Tyr Asp Thr Pro Lys
655             660             665             670 gct ggg aag cca ggt cta cct gcc cca gac gaa ttg gtg tac cag gtg     2256
Ala Gly Lys Pro Gly Leu Pro Ala Pro Asp Glu Leu Val Tyr Gln Val
        675             680             685 cca cag agc aca caa gaa gta tca gga gca gga agg gat ggg gaa tgt     2304
Pro Gln Ser Thr Gln Glu Val Ser Gly Ala Gly Arg Asp Gly Glu Cys
    690             695             700 gat gtt ttt aaa gaa atc ctt tga                                    2328
Asp Val Phe Lys Glu Ile Leu
            705

<210> SEQ ID NO 2
<211> LENGTH: 775
<212> TYPE: PRT
<213> ORGANISM: Homo sapiens

<400> SEQUENCE: 2

Met Ala Ser Arg Ala Val Val Arg Ala Arg Cys Pro Gln Cys Pro
1               5                   10                  15

Gln Val Arg Ala Ala Ala Ala Pro Ala Trp Ala Ala Leu Pro Leu
            20                  25                  30

Ser Arg Ser Leu Pro Pro Cys Ser Asn Ser Ser Phe Ser Met Pro
        35                  40                  45

Leu Phe Leu Leu Leu Leu Leu Val Leu Leu Leu Leu Glu Asp Ala
    50                  55                  60

Gly Ala Gln Gln Gly Asp Gly Cys Gly His Thr Val Leu Gly Pro Glu
65                  70                  75                  80

Ser Gly Thr Leu Thr Ser Ile Asn Tyr Pro Gln Thr Tyr Pro Asn Ser
                85                  90                  95

Thr Val Cys Glu Trp Glu Ile Arg Val Lys Met Gly Glu Arg Val Arg
            100                 105                 110

Ile Lys Phe Gly Asp Phe Asp Ile Glu Asp Ser Asp Cys His Phe
        115                 120                 125

Asn Tyr Leu Arg Ile Tyr Asn Gly Ile Gly Val Ser Arg Thr Glu Ile
    130                 135                 140

Gly Lys Tyr Cys Gly Leu Gly Leu Gln Met Asn His Ser Ile Glu Ser
145                 150                 155                 160
```

-continued

```
Lys Gly Asn Glu Ile Thr Leu Phe Met Ser Gly Ile His Val Ser
            165                 170                 175

Gly Arg Gly Phe Leu Ala Ser Tyr Ser Val Ile Asp Lys Gln Asp Leu
            180                 185                 190

Ile Thr Cys Leu Asp Thr Ala Ser Asn Phe Leu Glu Pro Glu Phe Ser
            195                 200                 205

Lys Tyr Cys Pro Ala Gly Cys Leu Leu Pro Phe Ala Glu Ile Ser Gly
            210                 215                 220

Thr Ile Pro His Gly Tyr Arg Asp Ser Ser Pro Leu Cys Met Ala Gly
225                 230                 235                 240

Val His Ala Gly Val Ser Asn Thr Leu Gly Gly Gln Ile Ser Val
            245                 250                 255

Val Ile Ser Lys Gly Ile Pro Tyr Tyr Glu Ser Ser Leu Ala Asn Asn
            260                 265                 270

Val Thr Ser Val Val Gly His Leu Ser Thr Ser Leu Phe Thr Phe Lys
            275                 280                 285

Thr Ser Gly Cys Tyr Gly Thr Leu Gly Met Glu Ser Gly Val Ile Ala
            290                 295                 300

Asp Pro Gln Ile Thr Ala Ser Ser Val Leu Glu Trp Thr Asp His Thr
305                 310                 315                 320

Gly Gln Glu Asn Ser Trp Lys Pro Lys Lys Ala Arg Leu Lys Lys Pro
            325                 330                 335

Gly Pro Pro Trp Ala Ala Phe Ala Thr Asp Glu Tyr Gln Trp Leu Gln
            340                 345                 350

Ile Asp Leu Asn Lys Glu Lys Lys Ile Thr Gly Ile Thr Thr Gly
            355                 360                 365

Ser Thr Met Val Glu His Asn Tyr Tyr Val Ser Ala Tyr Arg Ile Leu
            370                 375                 380

Tyr Ser Asp Asp Gly Gln Lys Trp Thr Val Tyr Arg Glu Pro Gly Val
385                 390                 395                 400

Glu Gln Asp Lys Ile Phe Gln Gly Asn Lys Asp Tyr His Gln Asp Val
            405                 410                 415

Arg Asn Asn Phe Leu Pro Pro Ile Ile Ala Arg Phe Ile Arg Val Asn
            420                 425                 430

Pro Thr Gln Trp Gln Gln Lys Ile Ala Met Lys Met Glu Leu Leu Gly
            435                 440                 445

Cys Gln Phe Ile Pro Lys Gly Arg Pro Lys Leu Thr Gln Pro Pro
            450                 455                 460

Pro Pro Arg Asn Ser Asn Asp Leu Lys Asn Thr Thr Ala Pro Pro Lys
465                 470                 475                 480

Ile Ala Lys Gly Arg Ala Pro Lys Phe Thr Gln Pro Leu Gln Pro Arg
            485                 490                 495

Ser Ser Asn Glu Phe Pro Ala Gln Thr Glu Gln Thr Thr Ala Ser Pro
            500                 505                 510

Asp Ile Arg Asn Thr Thr Val Thr Pro Asn Val Thr Lys Asp Val Ala
            515                 520                 525

Leu Ala Ala Val Leu Val Pro Val Leu Met Val Leu Thr Thr Leu
            530                 535                 540

Ile Leu Ile Leu Val Cys Ala Trp His Trp Arg Asn Arg Lys Lys Lys
545                 550                 555                 560

Thr Glu Gly Thr Tyr Asp Leu Pro Tyr Trp Asp Arg Ala Gly Trp Trp
            565                 570                 575
```

```
Lys Gly Met Lys Gln Phe Leu Pro Ala Lys Ala Val Asp His Glu Glu
            580                 585                 590
Thr Pro Val Arg Tyr Ser Ser Glu Val Asn His Leu Ser Pro Arg
        595                 600                 605
Glu Val Thr Thr Val Leu Gln Ala Asp Ser Ala Glu Tyr Ala Gln Pro
    610                 615                 620
Leu Val Gly Gly Ile Val Gly Thr Leu His Gln Arg Ser Thr Phe Lys
625                 630                 635                 640
Pro Glu Glu Gly Lys Glu Ala Gly Tyr Ala Asp Leu Asp Pro Tyr Asn
                645                 650                 655
Ser Pro Gly Gln Glu Val Tyr His Ala Tyr Ala Glu Pro Leu Pro Ile
            660                 665                 670
Thr Gly Pro Glu Tyr Ala Thr Pro Ile Ile Met Asp Met Ser Gly His
        675                 680                 685
Pro Thr Thr Ser Val Gly Gln Pro Ser Thr Ser Thr Phe Lys Ala Thr
    690                 695                 700
Gly Asn Gln Pro Pro Leu Val Gly Thr Tyr Asn Thr Leu Leu Ser
705                 710                 715                 720
Arg Thr Asp Ser Cys Ser Ser Ala Gln Ala Gly Tyr Thr Pro Lys
                725                 730                 735
Ala Gly Lys Pro Gly Leu Pro Ala Pro Asp Glu Leu Val Tyr Gln Val
            740                 745                 750
Pro Gln Ser Thr Gln Glu Val Ser Gly Ala Gly Arg Asp Gly Glu Cys
        755                 760                 765
Asp Val Phe Lys Glu Ile Leu
    770                 775

<210> SEQ ID NO 3
<211> LENGTH: 2328
<212> TYPE: DNA
<213> ORGANISM: Homo sapiens

<400> SEQUENCE: 3
atggcgagcc gggcggtggt gagagccagg cgctgcccgc agtgtcccca agtccgggcc      60
gcggccgccg ccccgccctg gccgcgctc cccctctccc gctccctccc tccctgctcc     120
aactcctcct ccttctccat gcctctgttc ctcctgctct tacttgtcct gctcctgctg     180
ctcgaggacg ctggagccca gcaaggtgat ggatgtggac acactgtact aggccctgag     240
agtggaaccc ttacatccat aaactaccca cagacctatc ccaacagcac tgtttgtgaa     300
tgggagatcc gtgtaaagat gggagagaga gttcgcatca aatttggtga ctttgacatt     360
gaagattctg attcttgtca ctttaattac ttgagaattt ataatggaat tggagtcagc     420
agaactgaaa taggcaaata ctgtggtctg gggttgcaaa tgaaccattc aattgaatca     480
aaaggcaatg aaatcacatt gctgttcatg agtggaatcc atgtttctgg acgcggattt     540
ttggcctcat actctgttat agataaacaa gatctaatta cttgtttgga cactgcatcc     600
aatttttttgg aacctgagtt cagtaagtac tgcccagctg gttgtctgct tccttttgct     660
gagatatctg gaacaattcc tcatggatat agagattcct cgccattgtg catggctggt     720
gtgcatgcag gagtagtgtc aaacacgttg gcggccaaat cagtgttgt aattagtaaa     780
ggtattccct attatgaaag ttctttggct aacaacgtca catctgtggt gggacactta     840
tctacaagtc ttttttacatt taagacaagt ggatgttatg gaacactggg gatggagtct     900
ggtgtgatcg cggatcctca aataacagca tcatctgtgc tggagtggac tgaccacaca     960
```

```
gggcaagaga acagttggaa acccaaaaaa gccaggctga aaaaacctgg accgccttgg    1020
gctgcttttg ccactgatga ataccagtgg ttacaaatag atttgaataa ggaaaagaaa    1080
ataacaggca ttataaccac tggatccacc atggtggagc acaattacta tgtgtctgcc    1140
tacagaatcc tgtacagtga tgatgggcag aaatggactg tgtacagaga gcctggtgtg    1200
gagcaagata agatatttca aggaaacaaa gattatcacc aggatgtgcg taataacttt    1260
ttgccaccaa ttattgcacg ttttattaga gtgaatccta cccaatggca gcagaaaatt    1320
gccatgaaaa tggagctgct cggatgtcag tttattccta aggtcgtcc tccaaaactt    1380 actcaacctc cacctcctcg gaacagcaat gacctcaaaa acactacagc ccctccaaaa    1440
atagccaaag gtcgtgcccc aaaatttacg caaccactac aacctcgcag tagcaatgaa    1500
tttcctgcac agacagaaca aacaactgcc agtcctgata tcagaaatac taccgtaact    1560
ccaaatgtaa ccaaagatgt agcgctggct gcagttcttg tccctgtgct ggtcatggtc    1620
ctcactactc tcattctcat attagtgtgt gcttggcact ggagaaacag aaagaaaaaa    1680
actgaaggca cctatgactt accttactgg gaccgggcag gttggtggaa aggaatgaag    1740
cagtttcttc ctgcaaaagc agtggaccat gaggaaaccc cagttcgcta tagcagcagc    1800
gaagttaatc acctgagtcc aagagaagtc accacagtgc tgcaggctga ctctgcagag    1860
tatgctcagc cactggtagg aggaattgtt ggtacacttc atcaaagatc tacctttaaa    1920
ccagaagaag gaaaagaagc aggctatgca gacctagatc cttacaactc accagggcag    1980
gaagtttatc atgcctatgc tgaaccactc ccaattacgg ggcctgagta tgcaacccca    2040
atcatcatgg acatgtcagg gcaccccaca acttcagttg gtcagccctc cacatccact    2100
ttcaaggcta cggggaacca acctcccccca ctagtgggaa cttacaatac acttctctcc    2160
aggactgaca gctgctcctc agcccaggcc cagtatgata ccccgaaagc tgggaagcca    2220
ggtctacctg ccccagacga attggtgtac caggtgccac agagcacaca agaagtatca    2280
ggagcaggaa gggatgggga atgtgatgtt tttaaagaaa tcctttga             2328

<210> SEQ ID NO 4
<211> LENGTH: 2310
<212> TYPE: DNA
<213> ORGANISM: Mus musculus
<220> FEATURE:
<221> NAME/KEY: sig_peptide
<222> LOCATION: (1)..(198)
<220> FEATURE:
<221> NAME/KEY: mat_peptide
<222> LOCATION: (199)..(2310)
<220> FEATURE:
<221> NAME/KEY: CDS
<222> LOCATION: (1)..(2310)

<400> SEQUENCE: 4 atg gcg agc cgg gcg ccg ctg aga gcc gcg cgc agc ccc cag ggt ccc     48
Met Ala Ser Arg Ala Pro Leu Arg Ala Ala Arg Ser Pro Gln Gly Pro
    -65             -60                 -55 gga ggc ccg gcc gcg ccc gcc gcc acc ggc cgg gcc gcg ctg ccc agc     96
Gly Gly Pro Ala Ala Pro Ala Ala Thr Gly Arg Ala Ala Leu Pro Ser
-50                 -45                 -40                 -35 gcc ggc tgc tgt ccc ctc cct cct ggc cgc aac tcc tcc tcc agg cct    144
Ala Gly Cys Cys Pro Leu Pro Pro Gly Arg Asn Ser Ser Ser Arg Pro
                -30                 -25                 -20 cga ctg ctc ctt ctg ctc ctc cta ctg ctc cag gac gct gga ggc cag    192
Arg Leu Leu Leu Leu Leu Leu Leu Leu Gln Asp Ala Gly Gly Gln
            -15                 -10                  -5
```

```
caa ggt gat gga tgt gga cac act gta cta ggc cct gag agt gga acc       240
Gln Gly Asp Gly Cys Gly His Thr Val Leu Gly Pro Glu Ser Gly Thr
 -1   1           5                  10 ctt aca tcc atc aac tac cca cat acc tat cct aac agc act gtg tgt       288
Leu Thr Ser Ile Asn Tyr Pro His Thr Tyr Pro Asn Ser Thr Val Cys
 15              20                  25                  30 gaa tgg gag att cga gtc agg acg gga gaa agg att cgc atc aaa ttc       336
Glu Trp Glu Ile Arg Val Arg Thr Gly Glu Arg Ile Arg Ile Lys Phe
                 35                  40                  45 ggt gac ttt gac att gaa gat tct gat tat tgt cac ctt aat tac ctg       384
Gly Asp Phe Asp Ile Glu Asp Ser Asp Tyr Cys His Leu Asn Tyr Leu
             50                  55                  60 aaa atc ttt aat gga att gga gtc agc aga acg gaa ata ggc aaa tac       432
Lys Ile Phe Asn Gly Ile Gly Val Ser Arg Thr Glu Ile Gly Lys Tyr
         65                  70                  75 tgt ggt ctg ggt tta caa atg aat cag tca att gag tcc aaa ggc agt       480
Cys Gly Leu Gly Leu Gln Met Asn Gln Ser Ile Glu Ser Lys Gly Ser
     80                  85                  90 gaa gtc aca gtg ctg ttc atg agt gga acc cat gct gct ggg cga gga       528
Glu Val Thr Val Leu Phe Met Ser Gly Thr His Ala Ala Gly Arg Gly
 95                  100                 105                 110 ttt ttg gct tca tac tca gtt ata gat aaa gaa gat tta atc act tgt       576
Phe Leu Ala Ser Tyr Ser Val Ile Asp Lys Glu Asp Leu Ile Thr Cys
                 115                 120                 125 ttg gat act gta tct aat ttt ttg gaa cca gag ttc agt aag tac tgc       624
Leu Asp Thr Val Ser Asn Phe Leu Glu Pro Glu Phe Ser Lys Tyr Cys
             130                 135                 140 cca gct ggc tgt ctt ttg cct ttt gct gaa ata tct gga aca att cct       672
Pro Ala Gly Cys Leu Leu Pro Phe Ala Glu Ile Ser Gly Thr Ile Pro
         145                 150                 155 cat gga tac aga gat tct tca cca ttg tgt atg gct gga atc cat gca       720
His Gly Tyr Arg Asp Ser Ser Pro Leu Cys Met Ala Gly Ile His Ala
     160                 165                 170 gga gta gtg tca aac gtg ctg ggt ggc caa atc agc att gtg att agc       768
Gly Val Val Ser Asn Val Leu Gly Gly Gln Ile Ser Ile Val Ile Ser
175                 180                 185                 190 aaa ggg acc cca tat tat gaa agc tct ttg gcc aac aat gtc act tcc       816
Lys Gly Thr Pro Tyr Tyr Glu Ser Ser Leu Ala Asn Asn Val Thr Ser
                 195                 200                 205 acg gtg gga tac tta tct gca agt ctg ttt aca ttt aag aca agt ggt       864
Thr Val Gly Tyr Leu Ser Ala Ser Leu Phe Thr Phe Lys Thr Ser Gly
             210                 215                 220 tgc tat ggg act ctg ggg atg gag tct ggt gtg att gcc gat ccc cag       912
Cys Tyr Gly Thr Leu Gly Met Glu Ser Gly Val Ile Ala Asp Pro Gln
         225                 230                 235 ata aca gca tcg tct gca ctg gag tgg act gac cac atg ggg cag gag       960
Ile Thr Ala Ser Ser Ala Leu Glu Trp Thr Asp His Met Gly Gln Glu
     240                 245                 250 aac agc tgg aca gcg gag aag gcc agg ctg aga aaa ccc ggg cct ccc      1008
Asn Ser Trp Thr Ala Glu Lys Ala Arg Leu Arg Lys Pro Gly Pro Pro
255                 260                 265                 270 tgg gct gct ttt gcc act gat gag cat cag tgg ctg cag ata gac ctt      1056
Trp Ala Ala Phe Ala Thr Asp Glu His Gln Trp Leu Gln Ile Asp Leu
                 275                 280                 285 aac aag gag aag aag ata aca ggt atc gta acc act ggg tct acc atg      1104
Asn Lys Glu Lys Lys Ile Thr Gly Ile Val Thr Thr Gly Ser Thr Met
             290                 295                 300 ata gaa cac agt tac tat gtg tct gcc tac aga gtc ctg tac agt gac      1152
Ile Glu His Ser Tyr Tyr Val Ser Ala Tyr Arg Val Leu Tyr Ser Asp
         305                 310                 315
```

```
gat ggg cag aga tgg act gtg tac aga gaa cct ggt gtg gac cag gac    1200
Asp Gly Gln Arg Trp Thr Val Tyr Arg Glu Pro Gly Val Asp Gln Asp
320                 325                 330 aag ata ttt caa gga aac aaa gat tat cac aag gat gtt cgt aat aac    1248
Lys Ile Phe Gln Gly Asn Lys Asp Tyr His Lys Asp Val Arg Asn Asn
335                 340                 345                 350 ttt ttg cca cca att att gca cgt ttc att aga gtg aac cct gtc cag    1296
Phe Leu Pro Pro Ile Ile Ala Arg Phe Ile Arg Val Asn Pro Val Gln
                355                 360                 365 tgg caa cag aaa att gcc atg aaa gtg gaa ctg ctc gga tgt cag ttt    1344
Trp Gln Gln Lys Ile Ala Met Lys Val Glu Leu Leu Gly Cys Gln Phe
        370                 375                 380 act ctc aaa ggt cgc ctt cca aag ctt act cca cct cct cgg aac ggc    1392
Thr Leu Lys Gly Arg Leu Pro Lys Leu Thr Pro Pro Pro Arg Asn Gly
385                 390                 395 aat aac ctc aga aat act aca gct cgt ccc aaa cta ggt aaa ggt cgt    1440
Asn Asn Leu Arg Asn Thr Thr Ala Arg Pro Lys Leu Gly Lys Gly Arg
    400                 405                 410 gcc cct aaa ttt act caa gtg ctc caa cct cga agt agg aat gaa ctt    1488
Ala Pro Lys Phe Thr Gln Val Leu Gln Pro Arg Ser Arg Asn Glu Leu
415                 420                 425                 430 cct gtg cag ccg gcg gag aca act acc act cct gat ata aaa aac acg    1536
Pro Val Gln Pro Ala Glu Thr Thr Thr Thr Pro Asp Ile Lys Asn Thr
                435                 440                 445 act gta act ccc agt gta acc aaa gat gtc gca ctg gct gcc gtt ctg    1584
Thr Val Thr Pro Ser Val Thr Lys Asp Val Ala Leu Ala Ala Val Leu
        450                 455                 460 gtc cct gtg ctg gtc atg gcc ctc acc aca ctc atc ctc att cta gtg    1632
Val Pro Val Leu Val Met Ala Leu Thr Thr Leu Ile Leu Ile Leu Val
                465                 470                 475 tgt gct tgg cac tgg aga aac agg aag aag aaa act gaa ggc gcc tat    1680
Cys Ala Trp His Trp Arg Asn Arg Lys Lys Lys Thr Glu Gly Ala Tyr
        480                 485                 490 gat tta ccc cac tgg gat cgg gca ggt tgg tgg aaa gga atg aag cag    1728
Asp Leu Pro His Trp Asp Arg Ala Gly Trp Trp Lys Gly Met Lys Gln
495                 500                 505                 510 ctt ctc cct gcc aag tcg gtg gac cac gag gag acg cca gtg cgc tac    1776
Leu Leu Pro Ala Lys Ser Val Asp His Glu Glu Thr Pro Val Arg Tyr
                515                 520                 525 agc act agt gaa gtc agt cac ctg agt gcc agg gaa gtc acc aca gtg    1824
Ser Thr Ser Glu Val Ser His Leu Ser Ala Arg Glu Val Thr Thr Val
        530                 535                 540 ctg cag gcc gac tct gca gaa tat gca cag ccc ctc gtg gga gga att    1872
Leu Gln Ala Asp Ser Ala Glu Tyr Ala Gln Pro Leu Val Gly Gly Ile
            545                 550                 555 gtt ggc aca ctc cat cag aga tcc acc ttt aaa cct gag gaa ggg aag    1920
Val Gly Thr Leu His Gln Arg Ser Thr Phe Lys Pro Glu Glu Gly Lys
        560                 565                 570 gaa gca ggc tat gca gac ctc gat cct tac aac tct cca atg cag gaa    1968
Glu Ala Gly Tyr Ala Asp Leu Asp Pro Tyr Asn Ser Pro Met Gln Glu
575                 580                 585                 590 gtg tac cac gcc tat gct gaa cca ctg ccc gta acg ggg cct gag tac    2016
Val Tyr His Ala Tyr Ala Glu Pro Leu Pro Val Thr Gly Pro Glu Tyr
                595                 600                 605 gca acc ccg atc gtc atg gac atg tca ggg cac ccc aca gcc tca gtt    2064
Ala Thr Pro Ile Val Met Asp Met Ser Gly His Pro Thr Ala Ser Val
        610                 615                 620 ggt ctg ccc tcc aca tcc acc ttc aaa act gca ggg acc cag cct cac    2112
Gly Leu Pro Ser Thr Ser Thr Phe Lys Thr Ala Gly Thr Gln Pro His
            625                 630                 635
```

```
gct tta gtg gga act tac aac act ctt ctc tcc agg act gac agc tgt    2160
Ala Leu Val Gly Thr Tyr Asn Thr Leu Leu Ser Arg Thr Asp Ser Cys
640                 645                 650 tcc tca ggc cag gct cag tat gac acc cca aaa ggt ggg aag tca gct    2208
Ser Ser Gly Gln Ala Gln Tyr Asp Thr Pro Lys Gly Gly Lys Ser Ala
655                 660                 665                 670 gct acc cca gag gaa ctg gta tac cag gtg ccc cag agc acc cag gag    2256
Ala Thr Pro Glu Glu Leu Val Tyr Gln Val Pro Gln Ser Thr Gln Glu
            675                 680                 685 cta tca gga gca gga agg gat gag aag ttt gat gct ttt aaa gaa atc    2304
Leu Ser Gly Ala Gly Arg Asp Glu Lys Phe Asp Ala Phe Lys Glu Ile
        690                 695                 700 ctt tga                                                             2310
Leu
```

<210> SEQ ID NO 5
<211> LENGTH: 769
<212> TYPE: PRT
<213> ORGANISM: Mus musculus

<400> SEQUENCE: 5

```
Met Ala Ser Arg Ala Pro Leu Arg Ala Ala Arg Ser Pro Gln Gly Pro
  1               5                  10                  15

Gly Gly Pro Ala Ala Pro Ala Ala Thr Gly Arg Ala Ala Leu Pro Ser
             20                  25                  30

Ala Gly Cys Cys Pro Leu Pro Pro Gly Arg Asn Ser Ser Ser Arg Pro
         35                  40                  45

Arg Leu Leu Leu Leu Leu Leu Leu Leu Gln Asp Ala Gly Gly Gln
     50                  55                  60

Gln Gly Asp Gly Cys Gly His Thr Val Leu Gly Pro Glu Ser Gly Thr
 65                  70                  75                  80

Leu Thr Ser Ile Asn Tyr Pro His Thr Tyr Pro Asn Ser Thr Val Cys
                 85                  90                  95

Glu Trp Glu Ile Arg Val Arg Thr Gly Glu Arg Ile Arg Ile Lys Phe
            100                 105                 110

Gly Asp Phe Asp Ile Glu Asp Ser Asp Tyr Cys His Leu Asn Tyr Leu
        115                 120                 125

Lys Ile Phe Asn Gly Ile Gly Val Ser Arg Thr Glu Ile Gly Lys Tyr
    130                 135                 140

Cys Gly Leu Gly Leu Gln Met Asn Gln Ser Ile Glu Ser Lys Gly Ser
145                 150                 155                 160

Glu Val Thr Val Leu Phe Met Ser Gly Thr His Ala Ala Gly Arg Gly
                165                 170                 175

Phe Leu Ala Ser Tyr Ser Val Ile Asp Lys Glu Asp Leu Ile Thr Cys
            180                 185                 190

Leu Asp Thr Val Ser Asn Phe Leu Glu Pro Glu Phe Ser Lys Tyr Cys
        195                 200                 205

Pro Ala Gly Cys Leu Leu Pro Phe Ala Glu Ile Ser Gly Thr Ile Pro
    210                 215                 220

His Gly Tyr Arg Asp Ser Ser Pro Leu Cys Met Ala Gly Ile His Ala
225                 230                 235                 240

Gly Val Val Ser Asn Val Leu Gly Gly Gln Ile Ser Ile Val Ile Ser
                245                 250                 255

Lys Gly Thr Pro Tyr Tyr Glu Ser Ser Leu Ala Asn Asn Val Thr Ser
            260                 265                 270
```

```
                    -continued

Thr Val Gly Tyr Leu Ser Ala Ser Leu Phe Thr Phe Lys Thr Ser Gly
            275                 280                 285

Cys Tyr Gly Thr Leu Gly Met Glu Ser Gly Val Ile Ala Asp Pro Gln
        290                 295                 300

Ile Thr Ala Ser Ser Ala Leu Glu Trp Thr Asp His Met Gly Gln Glu
305                 310                 315                 320

Asn Ser Trp Thr Ala Glu Lys Ala Arg Leu Arg Lys Pro Gly Pro Pro
                325                 330                 335

Trp Ala Ala Phe Ala Thr Asp Glu His Gln Trp Leu Gln Ile Asp Leu
            340                 345                 350

Asn Lys Glu Lys Lys Ile Thr Gly Ile Val Thr Thr Gly Ser Thr Met
            355                 360                 365

Ile Glu His Ser Tyr Tyr Val Ser Ala Tyr Arg Val Leu Tyr Ser Asp
370                 375                 380

Asp Gly Gln Arg Trp Thr Val Tyr Arg Glu Pro Gly Val Asp Gln Asp
385                 390                 395                 400

Lys Ile Phe Gln Gly Asn Lys Asp Tyr His Lys Asp Val Arg Asn Asn
                405                 410                 415

Phe Leu Pro Pro Ile Ile Ala Arg Phe Ile Arg Val Asn Pro Val Gln
            420                 425                 430

Trp Gln Gln Lys Ile Ala Met Lys Val Glu Leu Leu Gly Cys Gln Phe
            435                 440                 445

Thr Leu Lys Gly Arg Leu Pro Lys Leu Thr Pro Pro Pro Arg Asn Gly
        450                 455                 460

Asn Asn Leu Arg Asn Thr Thr Ala Arg Pro Lys Leu Gly Lys Gly Arg
465                 470                 475                 480

Ala Pro Lys Phe Thr Gln Val Leu Gln Pro Arg Ser Arg Asn Glu Leu
                485                 490                 495

Pro Val Gln Pro Ala Glu Thr Thr Thr Pro Asp Ile Lys Asn Thr
            500                 505                 510

Thr Val Thr Pro Ser Val Thr Lys Asp Val Ala Leu Ala Ala Val Leu
        515                 520                 525

Val Pro Val Leu Val Met Ala Leu Thr Thr Leu Ile Leu Ile Leu Val
    530                 535                 540

Cys Ala Trp His Trp Arg Asn Arg Lys Lys Lys Thr Glu Gly Ala Tyr
545                 550                 555                 560

Asp Leu Pro His Trp Asp Arg Ala Gly Trp Trp Lys Gly Met Lys Gln
                565                 570                 575

Leu Leu Pro Ala Lys Ser Val Asp His Glu Glu Thr Pro Val Arg Tyr
            580                 585                 590

Ser Thr Ser Glu Val Ser His Leu Ser Ala Arg Glu Val Thr Thr Val
            595                 600                 605

Leu Gln Ala Asp Ser Ala Glu Tyr Ala Gln Pro Leu Val Gly Gly Ile
    610                 615                 620

Val Gly Thr Leu His Gln Arg Ser Thr Phe Lys Pro Glu Glu Gly Lys
625                 630                 635                 640

Glu Ala Gly Tyr Ala Asp Leu Asp Pro Tyr Asn Ser Pro Met Gln Glu
                645                 650                 655

Val Tyr His Ala Tyr Ala Glu Pro Leu Pro Val Thr Gly Pro Glu Tyr
            660                 665                 670

Ala Thr Pro Ile Val Met Asp Met Ser Gly His Pro Thr Ala Ser Val
            675                 680                 685
```

```
Gly Leu Pro Ser Thr Ser Thr Phe Lys Thr Ala Gly Thr Gln Pro His
    690                 695                 700
Ala Leu Val Gly Thr Tyr Asn Thr Leu Leu Ser Arg Thr Asp Ser Cys
705                 710                 715                 720
Ser Ser Gly Gln Ala Gln Tyr Asp Thr Pro Lys Gly Gly Lys Ser Ala
                725                 730                 735
Ala Thr Pro Glu Glu Leu Val Tyr Gln Val Pro Gln Ser Thr Gln Glu
            740                 745                 750
Leu Ser Gly Ala Gly Arg Asp Glu Lys Phe Asp Ala Phe Lys Glu Ile
        755                 760                 765
Leu

<210> SEQ ID NO 6
<211> LENGTH: 2310
<212> TYPE: DNA
<213> ORGANISM: Mus musculus

<400> SEQUENCE: 6
atggcgagcc gggcgccgct gagagccgcg cgcagccccc agggtcccgg aggcccggcc      60
gcgcccgccg ccaccggccg ggccgcgctg cccagcgccg gctgctgtcc cctccctcct     120
ggccgcaact cctcctccag gcctcgactg ctccttctgc tgctcctact gctccaggac     180
gctggaggcc agcaaggtga tggatgtgga cacactgtac taggcccctga gagtggaacc     240 cttacatcca tcaactaccc acatacctat cctaacagca ctgtgtgtga atgggagatt     300
cgagtcagga cgggagaaag gattcgcatc aaattcggtg actttgacat tgaagattct     360
gattattgtc accttaatta cctgaaaatc tttaatggaa ttggagtcag cagaacggaa     420
ataggcaaat actgtggtct gggtttacaa atgaatcagt caattgagtc caaaggcagt     480
gaagtcacag tgctgttcat gagtggaacc catgctgctg gcgaggatt tttggcttca     540 tactcagtta tagataaaga agatttaatc acttgtttgg atactgtatc taattttttg     600
gaaccagagt tcagtaagta ctgcccagct ggctgtcttt tgccttttgc tgaaatatct     660
ggaacaattc ctcatggata cagagattct tcaccattgt gtatggctgg aatccatgca     720
ggagtagtgt caaacgtgct gggtggccaa atcagcattg tgattagcaa agggacccca     780

tattatgaaa gctcттттggc caacaatgtc acttccacgg tgggatactt atctgcaagt     840
ctgtttacat taagacaag tggttgctat gggactctgg ggatggagtc tggtgtgatt     900
gccgatcccc agataacagc atcgtctgca ctggagtgga ctgaccacat ggggcaggag     960
aacagctgga cagcggagaa ggccaggctg agaaaacccg ggcctccctg ggctgctttt    1020
gccactgatg agcatcagtg gctgcagata gaccttaaca aggagaagaa gataacaggt    1080
atcgtaacca ctgggtctac catgatagaa cacagttact atgtgtctgc ctacagagtc    1140
ctgtacagtg acgatgggca gatggactt gtgtacagag aacctggtgt ggaccaggac    1200
aagatatttc aaggaaacaa agattatcac aaggatgttc gtaataactt tttgccacca    1260

attattgcac gtttcattag agtgaaccct gtccagtggc aacagaaaat tgccatgaaa    1320
gtggaactgc tcgatgtcaa gtttactctc aaaggtcgcc ttccaaagct tactccacct    1380
cctcggaacg gcaataacct cagaaatact acagctcgtc ccaaactagg taaaggtcgt    1440
gcccctaaat ttactcaagt gctccaacct cgaagtagga atgaacttcc tgtgcagccg    1500
gcggagacaa ctaccactcc tgatataaaa aacacgactг taactcccag tgtaaccaaa    1560
gatgtcgcac tggctgccgt tctggtccct gtgctggtca tggccctcac cacactcatc    1620
```

```
ctcattctag tgtgtgcttg gcactggaga acaggaaga agaaaactga aggcgcctat      1680
gatttacccc actgggatcg ggcaggttgg tggaaaggaa tgaagcagct tctccctgcc      1740
aagtcggtgg accacgagga gacgccagtg cgctacagca ctagtgaagt cagtcacctg      1800
agtgccaggg aagtcaccac agtgctgcag gccgactctg cagaatatgc acagcccctc      1860
gtgggaggaa ttgttggcac actccatcag agatccacct ttaaacctga ggaagggaag      1920
gaagcaggct atgcagacct cgatccttac aactctccaa tgcaggaagt gtaccacgcc      1980
tatgctgaac cactgcccgt aacggggcct gagtacgcaa ccccgatcgt catggacatg      2040
tcagggcacc ccacagcctc agttggtctg ccctccacat ccaccttcaa aactgcaggg      2100
acccagcctc acgctttagt gggaacttac aacactcttc tctccaggac tgacagctgt      2160
tcctcaggcc aggctcagta tgacacccca aaggtgggaa agtcagctgc taccccagag      2220
gaactggtat accaggtgcc ccagagcacc caggagctat caggagcagg aagggatgag      2280
aagtttgatg ctttaaaga aatcctttga                                        2310

<210> SEQ ID NO 7
<211> LENGTH: 2310
<212> TYPE: DNA
<213> ORGANISM: Rattus rattus
<220> FEATURE:
<221> NAME/KEY: sig_peptide
<222> LOCATION: (1)..(198)
<220> FEATURE:
<221> NAME/KEY: mat_peptide
<222> LOCATION: (199)..(2310)
<220> FEATURE:
<221> NAME/KEY: CDS
<222> LOCATION: (1)..(2310)

<400> SEQUENCE: 7 atg gcg agc cgg gcg ccg ctg aga gcc gcg cgc agc ccg cag gat ccc         48
Met Ala Ser Arg Ala Pro Leu Arg Ala Ala Arg Ser Pro Gln Asp Pro
    -65                 -60                 -55 gga ggc cgg gcc gcg ccc gcc gcc acc ggc cgg gcc ccg ctg ccc agc         96
Gly Gly Arg Ala Ala Pro Ala Ala Thr Gly Arg Ala Pro Leu Pro Ser
-50                 -45                 -40                 -35 gcc ggc tgg tgt ccc ctc cct cct ggc cgc aac tcc tcc tcc agg cct        144
Ala Gly Trp Cys Pro Leu Pro Pro Gly Arg Asn Ser Ser Ser Arg Pro
                -30                 -25                 -20 cgg ctg ctc ctt cta ctg ctc cta ctg ctc ccg gac gct gga gcc cag        192
Arg Leu Leu Leu Leu Leu Leu Leu Leu Pro Asp Ala Gly Ala Gln
            -15                 -10                 -5 aaa ggt gat gga tgt gga cac act gta cta ggc cct gag agt gga acc        240
Lys Gly Asp Gly Cys Gly His Thr Val Leu Gly Pro Glu Ser Gly Thr
     -1   1               5                  10 ctt aca tcc atc aac tac cca cat acc tat cct aac agt act gtg tgt        288
Leu Thr Ser Ile Asn Tyr Pro His Thr Tyr Pro Asn Ser Thr Val Cys
 15                 20                  25                  30 aaa tgg gag att cga gta aag acg gga gaa aga att cgc atc aag ttc        336
Lys Trp Glu Ile Arg Val Lys Thr Gly Glu Arg Ile Arg Ile Lys Phe
                35                  40                  45 ggt gac ttt gac att gaa gat tct gat tat tgt cac ctt aat tac ctg        384
Gly Asp Phe Asp Ile Glu Asp Ser Asp Tyr Cys His Leu Asn Tyr Leu
                50                  55                  60 aaa atc ttt aat gga att gga gtc agc aga acg gaa ata ggc aag tac        432
Lys Ile Phe Asn Gly Ile Gly Val Ser Arg Thr Glu Ile Gly Lys Tyr
        65                  70                  75
```

```
tgt ggt ctg ggt tta caa atg aat cag tca att gag tcc aaa ggc agt     480
Cys Gly Leu Gly Leu Gln Met Asn Gln Ser Ile Glu Ser Lys Gly Ser
    80                  85                  90 gaa atc aca gtg ctg ttc atg agt gga atc cat gct tct ggt cga gga     528
Glu Ile Thr Val Leu Phe Met Ser Gly Ile His Ala Ser Gly Arg Gly
 95                 100                 105                 110 ttt ttg gct tct tac tca gtt ata gat aaa caa gat tta atc act tgt     576
Phe Leu Ala Ser Tyr Ser Val Ile Asp Lys Gln Asp Leu Ile Thr Cys
                    115                 120                 125 ttg gat act gta tct aat ttt ttg gaa cct gag ttc agt aag tac tgc     624
Leu Asp Thr Val Ser Asn Phe Leu Glu Pro Glu Phe Ser Lys Tyr Cys
                130                 135                 140 cca gct ggc tgt ctg ctg cct ttt gct gaa ata tct gga acg att cct     672
Pro Ala Gly Cys Leu Leu Pro Phe Ala Glu Ile Ser Gly Thr Ile Pro
            145                 150                 155 cat gga tat aga gat tct tca ccg ctg tgt atg gct gga atc cat gca     720
His Gly Tyr Arg Asp Ser Ser Pro Leu Cys Met Ala Gly Ile His Ala
        160                 165                 170 gga gta gtg tca gat gtg ctg ggt ggc caa atc agc gtt gtg att agc     768
Gly Val Val Ser Asp Val Leu Gly Gly Gln Ile Ser Val Val Ile Ser
175                 180                 185                 190 aaa ggc acc cca tat tac gaa agt tct ttg gcc aac aat gtc act tcc     816
Lys Gly Thr Pro Tyr Tyr Glu Ser Ser Leu Ala Asn Asn Val Thr Ser
                    195                 200                 205 atg gtg gga tac tta tct acg agt ctg ttt aca ttt aag aca agt ggt     864
Met Val Gly Tyr Leu Ser Thr Ser Leu Phe Thr Phe Lys Thr Ser Gly
                210                 215                 220 tgc tat ggg act cta ggg atg gag tca ggt gtg atc gcc gat ccc cag     912
Cys Tyr Gly Thr Leu Gly Met Glu Ser Gly Val Ile Ala Asp Pro Gln
            225                 230                 235 ata aca gca tca tct gta ctg gag tgg act gac cac atg ggg cag gag     960
Ile Thr Ala Ser Ser Val Leu Glu Trp Thr Asp His Met Gly Gln Glu
        240                 245                 250 aac agc tgg aaa ccc gag aag gcc agg ctg aga aaa ccg ggg cct ccc    1008
Asn Ser Trp Lys Pro Glu Lys Ala Arg Leu Arg Lys Pro Gly Pro Pro
255                 260                 265                 270 tgg gct gct ttt gcc act gat gag cat cag tgg ctg caa att gac ctt    1056
Trp Ala Ala Phe Ala Thr Asp Glu His Gln Trp Leu Gln Ile Asp Leu
                    275                 280                 285 aat aag gag aag aag ata aca ggc atc gta acc act gga tct acc ctg    1104
Asn Lys Glu Lys Lys Ile Thr Gly Ile Val Thr Thr Gly Ser Thr Leu
                290                 295                 300 ata gag cac aat tac tat gtg tct gcc tac aga gtt ctg tac agt gac    1152
Ile Glu His Asn Tyr Tyr Val Ser Ala Tyr Arg Val Leu Tyr Ser Asp
            305                 310                 315 gat ggg cag aaa tgg act gtg tac aga gag cct ggt gcg gct cag gac    1200
Asp Gly Gln Lys Trp Thr Val Tyr Arg Glu Pro Gly Ala Ala Gln Asp
        320                 325                 330 aag ata ttt caa gga aac aaa gat tat cac aag gat gtt cgt aat aac    1248
Lys Ile Phe Gln Gly Asn Lys Asp Tyr His Lys Asp Val Arg Asn Asn
335                 340                 345                 350 ttt ttg cca cca att att gca cgt ttc att aga gtg aac cct gtc cag    1296
Phe Leu Pro Pro Ile Ile Ala Arg Phe Ile Arg Val Asn Pro Val Gln
                    355                 360                 365 tgg caa cag aaa att gcc atg aaa gtg gaa ttg ctg gga tgt cag ttc    1344
Trp Gln Gln Lys Ile Ala Met Lys Val Glu Leu Leu Gly Cys Gln Phe
                370                 375                 380 act ctg aaa ggt cgc ctt cca aag ctt act caa cct ccc cca cct cgg    1392
Thr Leu Lys Gly Arg Leu Pro Lys Leu Thr Gln Pro Pro Pro Pro Arg
            385                 390                 395
```

```
aac agc aat aac ctc aaa aac act aca gtt cat ccc aaa cta ggt cgt        1440
Asn Ser Asn Asn Leu Lys Asn Thr Thr Val His Pro Lys Leu Gly Arg
    400             405                 410 gcc cct aaa ttt act caa gca ctc caa cca cga agt agg aat gac ctt        1488
Ala Pro Lys Phe Thr Gln Ala Leu Gln Pro Arg Ser Arg Asn Asp Leu
415                 420                 425                 430 cct ctg ctg ccg gcc cag aca act gcc act cct gat gtc aaa aac acg        1536
Pro Leu Leu Pro Ala Gln Thr Thr Ala Thr Pro Asp Val Lys Asn Thr
                435                 440                 445 act gtg act ccc agt gtg acc aaa gat gtt gca ctg gcc gcc gtt ctg        1584
Thr Val Thr Pro Ser Val Thr Lys Asp Val Ala Leu Ala Ala Val Leu
            450                 455                 460 gtt cct gtg ctg gtc atg gcc ctc acc aca ctc atc ctc att cta gtg        1632
Val Pro Val Leu Val Met Ala Leu Thr Thr Leu Ile Leu Ile Leu Val
        465                 470                 475 tgt gct tgg cat tgg aga aac aga aag aaa aaa gcc gaa ggc acc tat        1680
Cys Ala Trp His Trp Arg Asn Arg Lys Lys Lys Ala Glu Gly Thr Tyr
    480                 485                 490 gat tta ccc cac tgg gat cgg gca ggc tgg tgg aaa gga gtg aag cag        1728
Asp Leu Pro His Trp Asp Arg Ala Gly Trp Trp Lys Gly Val Lys Gln
495                 500                 505                 510 ctt ctc cct gcc aaa tcg gtg gaa cac gag gag acg cca gtg cgc tac        1776
Leu Leu Pro Ala Lys Ser Val Glu His Glu Glu Thr Pro Val Arg Tyr
                515                 520                 525 agc aac agt gaa gtt agt cac ctg agc ccg agg gaa gtc acg aca gtg        1824
Ser Asn Ser Glu Val Ser His Leu Ser Pro Arg Glu Val Thr Thr Val
            530                 535                 540 ctg caa gct gat tct gca gaa tac gca cag ccc ctc gtg gga gga att        1872
Leu Gln Ala Asp Ser Ala Glu Tyr Ala Gln Pro Leu Val Gly Gly Ile
        545                 550                 555 gtt ggc aca ctc cat cag aga tct acc ttt aaa cct gaa gaa gga aaa        1920
Val Gly Thr Leu His Gln Arg Ser Thr Phe Lys Pro Glu Glu Gly Lys
    560                 565                 570 gaa gcg agc tac gca gat cta gac ccc tac aac gct cca gta cag gaa        1968
Glu Ala Ser Tyr Ala Asp Leu Asp Pro Tyr Asn Ala Pro Val Gln Glu
575                 580                 585                 590 gtg tat cat gcc tac gct gag ccg ctg ccg gta acg ggg cct gag tac        2016
Val Tyr His Ala Tyr Ala Glu Pro Leu Pro Val Thr Gly Pro Glu Tyr
                595                 600                 605 gca acc cca atc gtc atg gac atg tca ggg cac tcc aca gcc tca gtt        2064
Ala Thr Pro Ile Val Met Asp Met Ser Gly His Ser Thr Ala Ser Val
            610                 615                 620 ggt ctg ccc tcc aca tcc act ttc aga act gca ggg aac cag cct ccc        2112
Gly Leu Pro Ser Thr Ser Thr Phe Arg Thr Ala Gly Asn Gln Pro Pro
        625                 630                 635 gca tta gtg gga act tac aac act ctt ctc tcc agg act gac agc tgt        2160
Ala Leu Val Gly Thr Tyr Asn Thr Leu Leu Ser Arg Thr Asp Ser Cys
    640                 645                 650 tcc tcg ggc cag gct cag tac gac acc cca aaa ggt ggg aag cca gca        2208
Ser Ser Gly Gln Ala Gln Tyr Asp Thr Pro Lys Gly Gly Lys Pro Ala
655                 660                 665                 670 gct gcc cca gag gaa ctg gtg tac cag gtg ccg cag agc acc cag gaa        2256
Ala Ala Pro Glu Glu Leu Val Tyr Gln Val Pro Gln Ser Thr Gln Glu
                675                 680                 685 gca tca gga gca gga agg gat gag aaa ttt gat gct ttt aaa gaa acc        2304
Ala Ser Gly Ala Gly Arg Asp Glu Lys Phe Asp Ala Phe Lys Glu Thr
            690                 695                 700 ctt tga                                                                 2310
Leu
```

<210> SEQ ID NO 8
<211> LENGTH: 769
<212> TYPE: PRT
<213> ORGANISM: Rattus rattus

<400> SEQUENCE: 8

```
Met Ala Ser Arg Ala Pro Leu Arg Ala Ala Arg Ser Pro Gln Asp Pro
 1               5                  10                  15

Gly Gly Arg Ala Ala Pro Ala Ala Thr Gly Arg Ala Pro Leu Pro Ser
            20                  25                  30

Ala Gly Trp Cys Pro Leu Pro Pro Gly Arg Asn Ser Ser Ser Arg Pro
        35                  40                  45

Arg Leu Leu Leu Leu Leu Leu Leu Leu Pro Asp Ala Gly Ala Gln
    50                  55                  60

Lys Gly Asp Gly Cys Gly His Thr Val Leu Pro Glu Ser Gly Thr
 65                  70                  75                  80

Leu Thr Ser Ile Asn Tyr Pro His Thr Tyr Pro Asn Ser Thr Val Cys
                85                  90                  95

Lys Trp Glu Ile Arg Val Lys Thr Gly Glu Arg Ile Arg Ile Lys Phe
            100                 105                 110

Gly Asp Phe Asp Ile Glu Asp Ser Asp Tyr Cys His Leu Asn Tyr Leu
        115                 120                 125

Lys Ile Phe Asn Gly Ile Gly Val Ser Arg Thr Glu Ile Gly Lys Tyr
    130                 135                 140

Cys Gly Leu Gly Leu Gln Met Asn Gln Ser Ile Glu Ser Lys Gly Ser
145                 150                 155                 160

Glu Ile Thr Val Leu Phe Met Ser Gly Ile His Ala Ser Gly Arg Gly
                165                 170                 175

Phe Leu Ala Ser Tyr Ser Val Ile Asp Lys Gln Asp Leu Ile Thr Cys
            180                 185                 190

Leu Asp Thr Val Ser Asn Phe Leu Glu Pro Glu Phe Ser Lys Tyr Cys
        195                 200                 205

Pro Ala Gly Cys Leu Leu Pro Phe Ala Glu Ile Ser Gly Thr Ile Pro
    210                 215                 220

His Gly Tyr Arg Asp Ser Ser Pro Leu Cys Met Ala Gly Ile His Ala
225                 230                 235                 240

Gly Val Val Ser Asp Val Leu Gly Gly Gln Ile Ser Val Ile Ser
                245                 250                 255

Lys Gly Thr Pro Tyr Tyr Glu Ser Ser Leu Ala Asn Asn Val Thr Ser
            260                 265                 270

Met Val Gly Tyr Leu Ser Thr Ser Leu Phe Thr Phe Lys Thr Ser Gly
        275                 280                 285

Cys Tyr Gly Thr Leu Gly Met Glu Ser Gly Val Ile Ala Asp Pro Gln
    290                 295                 300

Ile Thr Ala Ser Ser Val Leu Glu Trp Thr Asp His Met Gly Gln Glu
305                 310                 315                 320

Asn Ser Trp Lys Pro Glu Lys Ala Arg Leu Arg Lys Pro Gly Pro Pro
                325                 330                 335

Trp Ala Ala Phe Ala Thr Asp Glu His Gln Trp Leu Gln Ile Asp Leu
            340                 345                 350

Asn Lys Glu Lys Lys Ile Thr Gly Ile Val Thr Thr Gly Ser Thr Leu
        355                 360                 365

Ile Glu His Asn Tyr Tyr Val Ser Ala Tyr Arg Val Leu Tyr Ser Asp
    370                 375                 380
```

```
Asp Gly Gln Lys Trp Thr Val Tyr Arg Glu Pro Gly Ala Ala Gln Asp
385                 390                 395                 400

Lys Ile Phe Gln Gly Asn Lys Asp Tyr His Lys Asp Val Arg Asn Asn
                405                 410                 415

Phe Leu Pro Pro Ile Ile Ala Arg Phe Ile Arg Val Asn Pro Val Gln
            420                 425                 430

Trp Gln Gln Lys Ile Ala Met Lys Val Glu Leu Leu Gly Cys Gln Phe
        435                 440                 445

Thr Leu Lys Gly Arg Leu Pro Lys Leu Thr Gln Pro Pro Pro Arg
    450                 455                 460

Asn Ser Asn Asn Leu Lys Asn Thr Thr Val His Pro Lys Leu Gly Arg
465                 470                 475                 480

Ala Pro Lys Phe Thr Gln Ala Leu Gln Pro Arg Ser Arg Asn Asp Leu
                485                 490                 495

Pro Leu Leu Pro Ala Gln Thr Thr Ala Thr Pro Asp Val Lys Asn Thr
            500                 505                 510

Thr Val Thr Pro Ser Val Thr Lys Asp Val Ala Leu Ala Ala Val Leu
        515                 520                 525

Val Pro Val Leu Val Met Ala Leu Thr Thr Leu Ile Leu Ile Leu Val
    530                 535                 540

Cys Ala Trp His Trp Arg Asn Arg Lys Lys Lys Ala Glu Gly Thr Tyr
545                 550                 555                 560

Asp Leu Pro His Trp Asp Arg Ala Gly Trp Trp Lys Gly Val Lys Gln
                565                 570                 575

Leu Leu Pro Ala Lys Ser Val Glu His Glu Thr Pro Val Arg Tyr
            580                 585                 590

Ser Asn Ser Glu Val Ser His Leu Ser Pro Arg Glu Val Thr Thr Val
        595                 600                 605

Leu Gln Ala Asp Ser Ala Glu Tyr Ala Gln Pro Leu Val Gly Gly Ile
    610                 615                 620

Val Gly Thr Leu His Gln Arg Ser Thr Phe Lys Pro Glu Glu Gly Lys
625                 630                 635                 640

Glu Ala Ser Tyr Ala Asp Leu Asp Pro Tyr Asn Ala Pro Val Gln Glu
                645                 650                 655

Val Tyr His Ala Tyr Ala Glu Pro Leu Pro Val Thr Gly Pro Glu Tyr
            660                 665                 670

Ala Thr Pro Ile Val Met Asp Met Ser Gly His Ser Thr Ala Ser Val
        675                 680                 685

Gly Leu Pro Ser Thr Ser Phe Arg Thr Ala Gly Asn Gln Pro Pro
    690                 695                 700

Ala Leu Val Gly Thr Tyr Asn Thr Leu Leu Ser Arg Thr Asp Ser Cys
705                 710                 715                 720

Ser Ser Gly Gln Ala Gln Tyr Asp Thr Pro Lys Gly Lys Pro Ala
                725                 730                 735

Ala Ala Pro Glu Glu Leu Val Tyr Gln Val Pro Gln Ser Thr Gln Glu
            740                 745                 750

Ala Ser Gly Ala Gly Arg Asp Glu Lys Phe Asp Ala Phe Lys Glu Thr
        755                 760                 765

Leu

<210> SEQ ID NO 9
<211> LENGTH: 2310
<212> TYPE: DNA
<213> ORGANISM: Rattus rattus
```

<400> SEQUENCE: 9

```
atggcgagcc gggcgccgct gagagccgcg cgcagcccgc aggatcccgg aggccgggcc      60
gcgcccgccg ccaccggccg ggccccgctg cccagcgccg gctggtgtcc cctccctcct     120
ggccgcaact cctcctccag gcctcggctg ctccttctac tgctcctact gctcccggac     180
gctggagccc agaaaggtga tggatgtgga cacactgtac taggccctga gagtggaacc     240
cttacatcca tcaactaccc acatacctat cctaacagta ctgtgtgtaa atgggagatt     300
cgagtaaaga cgggagaaag aattcgcatc aagttcggtg actttgacat tgaagattct     360
gattattgtc accttaatta cctgaaaatc tttaatggaa ttggagtcag cagaacggaa     420
ataggcaagt actgtggtct gggtttacaa atgaatcagt caattgagtc caaaggcagt     480
gaaatcacag tgctgttcat gagtggaatc catgcttctg tcgaggatt tttggcttct      540
tactcagtta tagataaaca gatttaatc acttgtttgg atactgtatc taatttttg       600
gaacctgagt tcagtaagta ctgcccagct ggctgtctgc tgccttttgc tgaaatatct     660
ggaacgattc ctcatggata tagagattct tcaccgctgt gtatggctgg aatccatgca     720
ggagtagtgt cagatgtgct gggtggccaa atcagcgttg tgattagcaa aggcaccca      780
tattacgaaa gttctttggc caacaatgtc acttccatgg tgggatactt atctacgagt     840
ctgtttacat ttaagacaag tggttgctat gggactctag gatggagtc aggtgtgatc       900
gccgatcccc agataacagc atcatctgta ctggagtgga ctgaccacat ggggcaggag     960
aacagctgga aacccgagaa ggccaggctg agaaaaccgg ggcctccctg ggctgctttt    1020
gccactgatg agcatcagtg gctgcaaatt gaccttaata aggagaagaa gataacaggc    1080
atcgtaacca ctggatctac cctgatagag cacaattact atgtgtctgc ctacagagtt    1140
ctgtacagtg acgatgggca gaaatggact gtgtacagag agcctggtgc ggctcaggac    1200
aagatatttc aaggaaacaa agattatcac aaggatgttc gtaataactt tttgccacca    1260
attattgcac gtttcattag agtgaaccct gtccagtggc aacagaaaat tgccatgaaa    1320
gtggaattgc tgggatgtca gttcactctg aaaggtcgcc ttccaaagct tactcaacct    1380
cccccacctc ggaacagcaa taacctcaaa aacactacag ttcatcccaa actaggtcgt    1440
gccctaaat tactcaagc actccaacca cgaagtagga atgaccttcc tctgctgccg       1500
gcccagacaa ctgccactcc tgatgtcaaa aacacgactg tgactcccag tgtgaccaaa    1560
gatgttgcac tggccgccgt tctggttcct gtgctggtca tggccctcac cacactcatc    1620
ctcattctag tgtgtgcttg gcattggaga aacagaaaga aaaagccga aggcacctat     1680
gatttacccc actgggatcg ggcaggctgg tggaaaggag tgaagcagct tctccctgcc    1740
aaatcggtgg aacacgagga gacgccagtg cgctacagca acagtgaagt tagtcacctg    1800
agcccgaggg aagtcacgac agtgctgcaa gctgattctg cagaatacgc acagccctc    1860
gtgggaggaa ttgttggcac actccatcag agatctacct ttaaacctga gaaggaaaa    1920
gaagcgagct acgcagatct agacccctac aacgctccag tacaggaagt gtatcatgcc    1980
tacgctgagc cgctgccggt aacggggcct gagtacgcaa ccccaatcgt catggacatg    2040
tcagggcact ccacagcctc agttggtctg ccctccacat ccactttcag aactgcaggg    2100
aaccagcctc ccgcattagt gggaacttac aacactcttc tctccaggac tgacagctgt    2160
tcctcgggcc aggctcagta cgacaccca aaaggtggga agccagcagc tgccccagag    2220
gaactggtgt accaggtgcc gcagagcacc caggaagcat caggagcagg aagggatgag    2280
aaatttgatg cttttaaaga aaccctttga                                     2310
```

```
<210> SEQ ID NO 10
<211> LENGTH: 22
<212> TYPE: DNA
<213> ORGANISM: Mus musculus

<400> SEQUENCE: 10
ctgctccaac tcctcctcct tc                                              22

<210> SEQ ID NO 11
<211> LENGTH: 26
<212> TYPE: DNA
<213> ORGANISM: Mus musculus

<400> SEQUENCE: 11
ctgcttcatt cctttccacc aacctg                                          26

<210> SEQ ID NO 12
<211> LENGTH: 28
<212> TYPE: DNA
<213> ORGANISM: Rattus rattus

<400> SEQUENCE: 12
tgtgctggtc atggtcctca ctactctc                                        28

<210> SEQ ID NO 13
<211> LENGTH: 22
<212> TYPE: DNA
<213> ORGANISM: Rattus rattus

<400> SEQUENCE: 13
tgtgctttaa aacgatgctt tg                                              22

<210> SEQ ID NO 14
<211> LENGTH: 20
<212> TYPE: DNA
<213> ORGANISM: Mus musculus

<400> SEQUENCE: 14
gcactatgcg ggcggattgc                                                 20

<210> SEQ ID NO 15
<211> LENGTH: 24
<212> TYPE: DNA
<213> ORGANISM: Mus musculus

<400> SEQUENCE: 15
ggatgtaagg gttccactct cagg                                            24

<210> SEQ ID NO 16
<211> LENGTH: 17
<212> TYPE: PRT
<213> ORGANISM: Rabbit calicivirus

<400> SEQUENCE: 16

Gly Glu Arg Ile Arg Ile Lys Phe Gly Asp Gly Asp Ile Glu Asp Ser
 1               5                  10                  15

Asp

<210> SEQ ID NO 17
<211> LENGTH: 18
<212> TYPE: PRT
<213> ORGANISM: Rabbit calicivirus
```

<400> SEQUENCE: 17

Gln Asp Lys Ile Phe Gln Gly Asn Lys Asp Tyr His Lys Asp Val Arg
1               5                   10                  15

Asn Asn

<210> SEQ ID NO 18
<211> LENGTH: 24
<212> TYPE: PRT
<213> ORGANISM: Homo sapiens

<400> SEQUENCE: 18

Met Pro Met Gly Ser Leu Gln Pro Leu Ala Thr Leu Tyr Leu Leu Gly
1               5                   10                  15

Met Leu Val Ala Ser Val Leu Ala
            20

<210> SEQ ID NO 19
<211> LENGTH: 19
<212> TYPE: DNA
<213> ORGANISM: Homo sapiens

<400> SEQUENCE: 19
cccagcaagg tgatggatg                                                19

<210> SEQ ID NO 20
<211> LENGTH: 27
<212> TYPE: DNA
<213> ORGANISM: Homo sapiens

<400> SEQUENCE: 20
caagaatcag aatcttcaat gtcaaag                                       27

<210> SEQ ID NO 21
<211> LENGTH: 30
<212> TYPE: DNA
<213> ORGANISM: Homo sapiens

<400> SEQUENCE: 21
cctgagagtg gaacccttac atccataaac                                    30

<210> SEQ ID NO 22
<211> LENGTH: 19
<212> TYPE: DNA
<213> ORGANISM: Homo sapiens

<400> SEQUENCE: 22
gaaggtgaag gtcggagtc                                                19

<210> SEQ ID NO 23
<211> LENGTH: 20
<212> TYPE: DNA
<213> ORGANISM: Homo sapiens

<400> SEQUENCE: 23
gaagatggtg atgggatttc                                               20

<210> SEQ ID NO 24
<211> LENGTH: 20
<212> TYPE: DNA
<213> ORGANISM: Homo sapiens

```
-continued
<400> SEQUENCE: 24
caagcttccc gttctcagcc                                                20
```

POLYPEPTIDE ESDN, POLYNUCLEOTIDES ENCODING THE POLYPEPTIDE, AND UTILITY OF THE POLYPEPTIDE This is a Divisional of application Ser. No. 11/055,679 filed 11 Feb. 2005, which is a divisional of U.S. application Ser. No. 10/191,436, filed 10 Jul. 2002, which claims benefit to Japanese Application No. 2001-397725, filed 27 Dec. 2001, which are incorporated herein by reference.

FIELD OF THE INVENTION

The invention is related to a new polypeptide called Endothelial and Smooth muscle cell-Derived Neuropilin-like molecule hereinafter, simply referred to as "ESDN"), the preparation process, CDNA encoding ESDN, a vector containing the cDNA, host cells transformed by the vector, an antibody of ESDN, pharmaceutical compositions containing the polypeptide or the antibody, methods and reagents of measuring the quantity of ESDN, screening methods using ESDN.

BACKGROUND OF THE INVENTION

Since isolation of vascular endothelial growth factor (VEGF), the complicated network of extracellular signal transduction in angiopoiesis has been drastically elucidated. Research in to mice which has a targeted mutation for the tyrosine kinase, for example, this ligand, Flk-1/VEGFR2, and Flt-1/VEGFR1, etc. was a first key point related the first step of angiopoiesis and vascularization.

VEGF receptor-2(VEGFR-2) is necessary in endothelial formation and a targeted mutation for this gene resulted in a shortage of blood cells or organized blood vessels and death in the embryo at 9.5 days post-coitum. However, according to analysis of early marker by RT-PCR revealing early hemopoiesis and the report that endothelial precursory cell was actually formed in absence of VEGFR-2, it is suggested that VEGFR-2 is required for the growth later, but not absolutely essential for hematoblast formation.

VEGF receptor-1 (VEGFR-1) knock-out mice were also dead in the embryo at 9.5 days post-coitum, but differentiation of their endothelial cells was not influenced directly. Instead, it is speculated that movement of the mesenchyme hematoblasts maybe stagnant generally and that their over-crowded endothelial precursory cells may result in destroying vascular system severely.

VEGF knock-out mice were also dead in the embryo at 9.5 days post-coitum conspicuously, and differentiation of their endothelial cells were not defective. That is, substantially, it was the same to VEGF-1 knock-out mice, but the phenotype was slighter than that of VEGF-1 knock-out mice. The conspicuous characteristic related to a targeted mutation within this gene was that gene deletion of the heterozygote was lethal to the mouse embryo at 11.5 days post-coitum. This revealed that development in the embryo may depend strictly on the quantity of VEGF expression.

Other tyrosine kinase receptors, such as Tie-2 and its ligand, are specifically expressed in vascular endothelial cells, contributing to the step of vascularization in the late stage of angiopoiesis. Though destruction of these genes, which does not have any influence on angiopoiesis, affects vessel remodeling to cause death in the embryo at 10.5 days post-coitum. They play some roles in interaction between endothelial cells and their surrounding vascular smooth muscle cells(VSMC) or mesenchyme cells. In addition to the system specific to vascular, PDGF-BB, TGF-β and their receptors also play similar roles in interaction between endothelial cells and their surrounding cells. Investigations into the relationship between vascular system and neuropilin-1 (NP-1) which was cloned as an antigen recognized by the monoclonal antibody recognizing the first developed neuron led this field to a new phase.

Then, identification as a receptor of semaphorin 3A (sema3A) has come to attract attention in relation to axon formation, and search for other VEGF receptors led to discovery of NP-1 which is also a co-receptor for VEGFR-2. NP-1 enhances not only the binding to one isoform of VEGF-2, but also chemotaxis and probable mitosis of endothelial cells. Before this identification, it was revealed that chimerical mice over-expressing NP-1 presented the phenotype of hypertrophic vascular formation. NP-1 knock-out mice presented the phenotype of low angiogenesis in the central nervous system and large vascular variations. On the other hand, it has not been reported whether sema3A knock-out mice presented the abnormal vessels, while it is interesting that these mice presented the phenotype of thin myocardium, which was also observed in mice over-expressing NP-1.

Another example is the Eph/Ephrin system, which was first studied extensively in the neurological field. Later, this system was re-identified as an only surface marker discriminating arteries and veins. They are expressed in mesenchyme cells which surround the vessels and contact with endothelial cells. Speculating that there are many extracellular signal transduction molecules in vessels besides the above molecules, the inventors have suggested that proving this speculation would contribute to more understanding of this complex system.

DISCLOSURE OF THE INVENTION

The present inventors have directed their attention and have carried out energetic researches in order to find useful and novel factors (polypeptides) which play an important role for morbid vascular smooth muscle in restenosis after percutaneous transluminal coronany angioplasty (PTCA) and arterial sclerosis in the field of cardiovascular system, especially secretory and membrane protein containing signal sequence.

Conventionally, when a man skilled in the art intends to obtain a particular polypeptide or a cDNA encoding it, he generally utilizes methods by confirming an intended biological activity in a tissue or in a cell medium, isolating and purifying the polypeptide and then cloning a gene or methods by "expression-cloning" with the guidance of the biological activity.

However, physiologically active polypeptides in living body have often many kinds of activities Therefore, a gene which was cloned with the guidance of a certain activity often turns to be identical to one encoding a polypeptide already known. Moreover, in bone marrow stromal cells, many of factors are expressed in a very small amount or only under specific physiological conditions, which makes it difficult to isolate and purify of the factor and to confirm its biological activity.

The present inventors have studied methods for cloning genes coding proliferation and/or differentiation factors functioning in hematopoietic systems and immune systems. Focusing their attention on the fact that most of the secretory proteins such as proliferation and/or differentiation factors (for example various cytokines) and membrane proteins such as receptors thereof (hereafter these proteins will be referred to generally as secretory proteins and the like) have sequences called signal peptides in the N-termini, the inventors conducted extensive studies on a process for efficiently and selectively cloning a gene coding for a signal peptide. Finally, the present inventors have successfully invented a screening method for cDNAs having sequence encoding signal peptides and named the method signal sequence trap method (hereinafter, simply referred to as "SST") (See Japanese Patent Application No. 6-13951). The present inventors have also developed yeast SST method on the same concept. By the method using yeast, genes including sequence encoding signal peptide can be identified more easily and effectively (See U.S. Pat. No. 5,536,637).

By using newly amended SST method, the present inventors have achieved isolation of a novel membrane protein produced by vascular cell. The protein of the invention, called ESDN, is a novel type-I transmembrane protein and contains characteristic domains like neuropilin.

As it may be explained in detail subsequently, since ESDN of the present invention is expressed in coronary cells and smooth muscle cells, and in artery smooth muscle cells and tunica media of carotid artery after ballon injury, it is suggested that ESDN of the present invention is useful for treatments in restenosis after PTCA and arterial sclerosis in the field of cardiovascular system.

The CDNA sequence of the invention was identified as the human ESDN shown in SEQ ID NO. 2. Based on the information obtained from the yeast SST method, it was isolated from cDNA libraries constructed from primary culture of human coronary arterial cells and smooth muscle cells. The human ESDN clone shown in SEQ ID NO. 3 is the full-length cDNA containing complete sequence of cDNA coding the secretory protein(shown as the human ESDN protein herein).

The cDNA sequence of the invention was identified as the mouse ESDN shown in SEQ ID NO. 6. Based on the information obtained from the yeast SST method, it was isolated from mouse cDNA libraries. The mouse ESDN clone shown in SEQ ID NO. 5 is the full-length CDNA containing complete sequence of CDNA coding the secretory protein (shown as the mouse ESDN protein herein).

The cDNA sequence of the invention was identified as the rat ESDN shown in SEQ ID NO. 9. Based on the information obtained from the yeast SST method, it was isolated from rat cDNA libraries. The rat ESDN clone shown in SEQ ID NO. 8 is the full-length CDNA containing complete sequence of cDNA coding the secretory protein (shown as the rat ESDN protein herein).

At GeneBank and NCBI, the rat polypeptide of the invention and the nuclear acid sequence coding the polypeptide were compared by BLASTN, FASTA, and UNIGENE searches to known nuclear acid sequences registered in nucleotide sequence data bases, or by BLASTP, FLy Database, SwissProt searches to amino acid sequences of known polypeptide registered in amino acid sequence data bases. As a result, there was no sequence which corresponded to rat ESDN as the polypeptide of the present invention and nuclear acid sequence coding the polypeptide, so that it was found out that the polypeptide of the invention is a novel secretory protein.

DETAILED DESCRIPTION OF THE INVENTION

Figures 1, 2, 3:
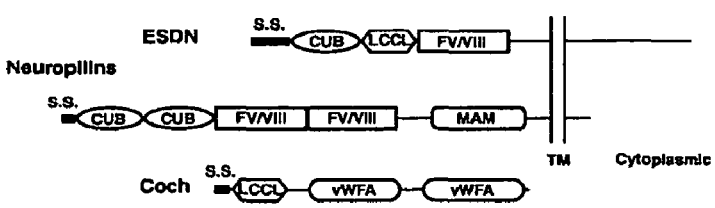
FIG. 1 shows an alignment of human, mouse and rat ESDNs.
FIG. 2 shows a schematic view of the respective domain structures in ESDN, neuropilin and Coch.
FIG. 3 shows an alignment of respective LCCL modules from human, mouse, or rat ESDN, Limulus factor C, two LCCL domains of predicted rat Lgl-1, and human, mouse, or chicken Coch.
Figure 4:
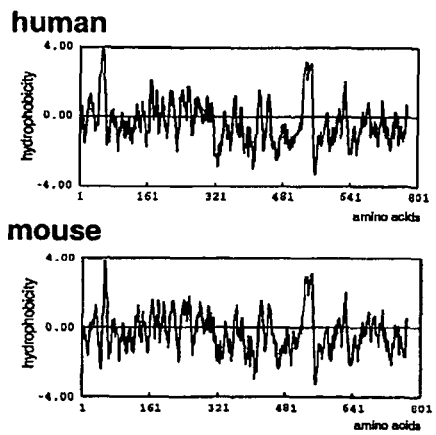
FIG. 4 shows hydrophobicity profiles of human and mouse ESDNs.

The invention provides:
(1) A substantially purified form of a polypeptide comprising one of amino-acid sequences shown in SEQ ID NO. 2, 5 or 8, or homologue thereof, fragment thereof, or a polypeptide comprising homologue of the fragment.
(2) A polypeptide according to (1), comprising the amino-acid sequence shown in SEQ ID NO. 2, 5 or 8.
(3) A cDNA encoding the polypeptide according to (1) or (2).
(4) AcDNA according to (3) comprising the nucleotide sequence shown in SEQ ID NO. 3, 6 or 9, or a fragment cDNA selectively hybridized to the sequence.
(5) A replication or expression vector carrying the cDNA according to (3) to (4).
(6) A host cell transformed with the replication or expression vector according to (5).
(7) A method for producing the polypeptide according to (1) or (2) which comprises culturing a host cell according to (6) under a condition effective to express the polypeptide according to (1) or (2).
(8) A monoclonal or polyclonal antibody against the polypeptide according to (1) or (2).
(9) A pharmaceutical composition containing the polypeptide according to (1) or (2) or the antibody according to (8), in association with pharmaceutically acceptable diluent and/or carrier.
(10) A pharmaceutical composition which is therapeutically effective in treatment for restenosis after PTCA, and containing the polypeptide according to (1) or (2) or the antibody according to (8), in association with pharmaceutically acceptable diluent and/or carrier.
(11) The pharmaceutical composition described in above (10), which is therapeutically effective in treatment for arterial sclerosis, and containing the polypeptide according to (1) or (2) or the antibody according to (8), in association with pharmaceutically acceptable diluent and/or carrier.
(12) A method for measuring the quantity of the polypeptide according to (1) or (2).

(13) A immunochemical method for measuring the quantity of the polypeptide according to (1) or (2), comprising using the antibody according to (8).

(14) A reagent for detecting the polypeptide according to (1) or (2), which is used in the method according to (12) or (13)

(15) A reagent for examining restenosis after PTCA by the method according to (12) or (13).

(16) A reagent for examining arterial sclerosis, which is used in the method according to (12) or (13).

(17) A screening method for selecting reagents having antagonistic or agonistic activity against the polypeptide, comprising using the polypeptide according to (1) or (2).

The selectively hybridizing cDNAs contain complementary sequences against above sequence. The hybridization on stringent condition is preferred.

Generally, a polypeptide comprising amino acid sequence shown in SEQ ID NO. 2, 5 or 8 in substantially purified form means a polypeptide comprising the amino acid sequence No.2, 5 or 8 in 90% or more, e.g. 95%, 98% or 99%, in the preparation.

A homologue of polypeptide comprising amino acid sequence shown in SEQ ID NO. 2, 5 or 8 is generally at least 70%, preferably at least 80 or 90% and more preferably at least 95% homologous to the polypeptide over a region of at least 20, preferably at least 30, for instance 40, 60, 80 or 100 more contiguous amino acids. Such a polypeptide homologue is referred to as a polypeptide of the present invention.

Generally, a fragment of polypeptide comprising amino acid sequence shown in SEQ ID NO. 2, 5 or 8, or a fragment of its homologues is at least 10, preferably at least 15, for example 20, 25, 30, 40, 50 or 60 amino acids in length, and is also referred to as polypeptide of the present invention.

A CDNA capable of selectively hybridizing to the DNA comprising nucleotide sequence shown in SEQ ID NO. 3, 6 or 9 is generally at least 70%, preferably at least 80 or 90% and more preferably at least 95% homologous to the CDNA comprising nucleotide sequence shown in SEQ ID NO. 3, 6 or 9 over a region of at least 20, preferably at least 30 or more, for instance 40, 60, 80 or 100, contiguous nucleotides. Such a CDNA is referred to as CDNA of the present invention.

Fragments of the DNA comprising nucleotide sequence shown in SEQ ID NO. 3, 6 or 9 are at least 10, preferably at least 15, for example 20, 25, 30 or 40 nucleotides in length, and are also referred to as cDNA of the present invention as used herein.

A further embodiment of the present invention provides replication and expression vectors carrying CDNA of the present invention. The vectors may be, for example, plasmid, virus or phage vectors provided with an origin of replication, optionally a promoter for the expression of the said CDNA and optionally a regulator of the promoter. The vector may contain one or more selectable marker genes, for example a ampicillin resistance gene. The vector may be used in vitro, for example, in production of RNA corresponding to the CDNA and in transfection of a host cell.

A further embodiment of the invention provides host cells transformed with the vectors for the replication and expression of the DNA of the invention, including the DNA SEQ ID NO. 3, 6 or 9 or the open reading frame thereof. The cells will be chosen to be compatible with the vector and may for example be bacterial, yeast, insect or mammalian.

A further embodiment of the present invention provides a method for producing a polypeptide which comprises culturing host cells of the present invention under conditions effective to express a polypeptide of the present invention. Preferably, in addition, such a method is carried out under conditions in which the polypeptide of the invention is expressed and then produced from the host cells.

The cDNA of the present invention may also be inserted into the vectors described above in an antisense orientation in order to prove for production of antisense RNA. Such antisense RNA may be used in controlling the level of the polypeptide of the present invention in a cell.

The present invention also provides monoclonal or polyclonal antibodies against a polypeptide of the present invention. The present invention further provides a process for production of monoclonal or polyclonal antibodies to the polypeptides of the present invention. Monoclonal antibodies may be prepared by common hybridoma technology using polypeptides of the present invention or fragments thereof as an immunogen. Polyclonal antibodies may also be prepared by common means which comprises inoculating host animals, for example a rat or a rabbit, with polypeptides of the invention and recovering immune serum.

The present invention also provides pharmaceutical compositions containing a polypeptide of the present invention, or an antibody thereof, in association with a pharmaceutically acceptable diluent and/or carrier.

As the polypeptide of the present invention, those which have deficiency in a part of their amino acid sequence (e.g., a polypeptide comprised of the only essential sequence for revealing a biological activity in an amino acid sequence shown in SEQ ID NO. 2), those which have a part of their amino acid sequence replaced by other amino acids (e.g., those replaced by an amino acid having a similar property) and those which have other amino acids added or inserted into a part of their amino acid sequence, as well as those comprising the amino acid sequence shown in SEQ ID NO. 2, 5 or 8.

As known well, there are one to six kinds of codon encoding one amino acid (for example, one kind of codon for Methionine (Met), and six kinds of codon for leucine (Leu) are known). Accordingly, the nucleotide sequence of cDNA can be changed without changing the amino acid sequence of the polypeptide.

The cDNA of the present invention includes every group of nucleotide sequences encoding polypeptides shown in SEQ ID NO. 2, 5 or 8. There is a probability that yield of a polypeptide is improved by changing a nucleotide sequence.

The cDNA specified in SEQ ID NO. 3, 6 or 9 is an embodiment of the DNA shown in SEQ ID NO. 2, 5 or 8, and indicates the sequence of natural form.

A cDNA carrying nucleotide sequence shown in SEQ ID NO. 3, 6 or 9 is prepared by the following method:

First, Yeast SST method (see U.S. Pat. No. 5,536,637) is briefly described below.

Yeast such as Saccharomyces cerevisiae should secrete invertase into the medium in order to take sucrose or raffinose as a source of energy or carbon (Invertase is an enzyme to cleave raffinose into sucrose and melibiose, sucrose into fructose and glucose.). It is known that many of known mammalian signal sequences make yeast secrete its invertase.

From this knowledge, SST method was developed as a screening method to find novel signal sequence which enables invertase secretion of yeast from mammalian cDNA library with growth of the yeast as index.

Non-secretory type invertase gene SUC2 (GENBANK Accession No. V01311) lacking initiation codon ATG was inserted to yeast expression vector to prepare yeast SST vector pSUC2. In this expression vector, ADH promoter, ADH terminator (both were derived from AAH5 plasmid (Gammerer, Methods in Enzymol. 101, 192-201, 1983)), 2 µ ori (as a yeast replication origin), TRP1 (as a yeast selective marker), ColE1 ori(as a *E. Coli* replication origin) and ampicillin resistance gene (as a drug resistance marker) were inserted. Mammalian cDNA was inserted into the upstream of SUC2 gene to prepare yeast SST CDNA library. Yeast lacking secretory type invertase, was transformed with this library.

If inserted mammalian cDNA encodes a signal peptide, the yeast could survive in raffinose medium as a result of restoring secretion of invertase. By culturing yeast in colonies to prepare plasmids and determine the nucleotide sequence of the insert cDNAs, it is possible to identify novel signal peptide rapidly and easily.

Preparation of yeast SST cDNA library is as follows:
(1) mRNA is isolated from the targeted cells, a double-strand cDNA is synthesized by using random primer with certain restriction enzyme (enzyme I) recognition site,
(2) the double-strand cDNA is ligated to adapter containing certain restriction endonuclease (enzyme II) recognition site different from enzyme I, digested with enzyme I and fractionated in a appropriate size,
(3) the obtained cDNA fragment is inserted into yeast expression vector on the upstream region of invertase gene of which signal peptide is deleted and the library is transformed.

Detailed description of each step is as follows: In step (1), mRNA is isolated from mammalian organs and cell lines after stimulating them with appropriate stimulator if necessary by known methods (as described in Molecular Cloning (Sambrook, J., Fritsch, E. F. and Maniatis, T., Cold Spring Harbor Laboratory Press, 1989) or Current Protocol in Molecular Biology (F. M. Ausubel et al, John Wiley & Sons, Inc.)) unless otherwise specified.

A suitable tissue may be heart of fetal mouse. Double-strand cDNA synthesis using random primer is performed by known methods.

Any sites may be used as restriction endonuclease recognition site I which is linked to adapter and restriction endonuclease recognition site II which is used in step (2), insofar as both sites are different each other. Preferably, XhoI is used as enzyme I and EcoRI as enzyme II.

In step (2), ends of cDNA are blunted with T4DNA polymerase, and ligated to enzyme II adapter and digested with enzyme I. Fragment cDNA is analyzed with agarose-gel electrophoresis (AGE) and cDNA fraction ranging in size from 300 to 800 bp is selected. As mentioned above, any enzyme may be used as enzyme II insofar as it is not same with the enzyme I.

In step (3), cDNA fragment obtained in step (2) is inserted into yeast expression vector on the upstream region of invertase gene of which signal peptide is deleted. *E. coli* transformed with the expression vector Many vectors are known as yeast expression plasmid vector. For example, YEp24 is also functioned in *E. Coli*. Preferably pSUC2 as described above is used.

Many host *E. Coli* strains are known as usable for transformation, preferably DH10B competent cell is used. Any known transformation method is available, preferably it is performed by electropolation method. Transformant is cultured by conventional methods to obtain cDNA library for yeast SST method.

However, not all of the cloned cDNA fragment are introduced into this cDNA library. Further, not all of the gene fragments encode unknown(novel) signal peptides. It is therefore necessary to screen a gene fragment encoding for an unknown signal peptide from the library.

Therefore, screening of fragments containing a sequence encoding an appropriate signal peptide is performed by transformation of the cDNA library into Saccharomyces cerevisiae (e.g. YT455 strain) lacking the invertase gene or strain which artificially lack the gene(it may be prepared by known methods.). Transformation of yeast is performed by known methods, e.g. lithium acetate method. Transformant is cultured in a selective medium, then transferred to a medium containing raffinose as a carbon source. Survival colonies are selected and then plasmid is collected. Survival colonies on a raffinose-medium indicates that some signal peptide of secretory protein was inserted to this clone.

With respect to isolated positive clones, the nucleotide is determined. As to a CDNA encoding unknown protein, full-length clone may be isolated by using cDNA fragment as a probe, and then the full-length nucleotide sequence is determined. The manipulation is performed by known methods.

Once the nucleotide sequences shown in SEQ ID NO. 3, 6 or 9 are determined partially or preferably fully, it is possible to obtain cDNA encoding mammalian protein itself, homologue or subset. By screening cDNA library or mRNA derived from mammals by PCR method with any synthesized oligonucleotide primers or by hybridization with any fragment as a probe, it is possible to obtain cDNA encoding other mammalian homologue protein from other mammalian cDNA or genome library.

If the cDNA obtained above contains a nucleotide sequence of cDNA fragment obtained by SST (or consensus sequence thereof), it implies that the cDNA encodes signal peptide. Accordingly, it is clear that the length of the cDNA is full or almost full. (All signal sequences exist at N-termini of a protein and are encoded at 5'-termini of open reading frame of cDNA.)

By known methods, the confirmation of full-length may be carried out by Northern analysis with the said cDNA as a probe. The cDNA is assumed to have almost complete length if the length of the cDNA is almost the same with the length of the mRNA obtained in the hybridizing band.

The present invention provides both types of protein, i.e., full-length and mature. The full-length proteins are specified with the amino acid sequences translated from the nucleotides shown in SEQ ID NO. 2, 5 or 8. The mature proteins are obtained by expression in suitable mammal cells or other host cells transformed by the full-length DNA shown in SEQ ID NO. 3, 6 or 9. Sequences of mature proteins could be predicted from full-length amino acid sequences. (Shown in FIG. 1) Once the nucleotide sequences shown in SEQ ID Nos. 3, 6 or 9 are determined, cDNAs of the present invention are obtained by chemical synthesis, or by hybridization making use of nucleotide fragments which are chemically synthesized as a probe. Furthermore, cDNAs of the invention are obtained in desired amount by transforming a vector that contains the DNA into a proper host, and culturing the transformant.

The polypeptides of the present invention may be prepared by:
(1) isolating and purifying from an organism or a cultured cell,
(2) chemically synthesizing, or
(3) using recombinant DNA technology, preferably, by the method described in (3) in an industrial production.

Examples of expression system (host-vector system) for producing a polypeptide by using recombinant DNA technology are the expression systems of bacteria, yeast, insect cells and mammalian cells.

In the expression of the polypeptide, for example, in *E. Coli*, the expression vector is prepared by adding the initiation codon (ATG) to 5' end of acDNA encoding mature peptide, connecting the cDNA thus obtained to the downstream of a proper promoter (e.g., trp promoter, lac promoter, λ PL promoter, and T7 promoter), and then inserting it into a vector (e.g., pBR322, pUC18 and pUC19 ) which functions in an *E. coli* strain.

Then, an *E. coli* strain (e.g., *E. coli* DH1 strain, *E. coli* JM109 strain and *E. coli* HB101 strain) which is transformed with the expression vector described above may be cultured in a appropriate medium to obtain the desired polypeptide. When a signal peptide of bacteria (e.g., signal peptide of pel B) is utilized, the desired polypeptide may be also released in periplasm. Furthermore, a fusion protein with other polypeptide may be also produced easily.

In the expression of the polypeptide, for example, in mammalian cells, for example, the expression vector is prepared by inserting the DNA encoding nucleotide shown in SEQ ID NO. 3, 6 or 9 into the downstream of a proper promoter (e.g., SV40 promoter, LTR promoter and metallothionein promoter) in a proper vector (e.g., retrovirus vector, papilloma virus vector, vaccinia virus vector and SV40 vector). A proper mammalian cell (e.g., monkey COS-1 cell, COS-7 cell, Chinese hamster CHO cell, mouse L cell etc.) is transformed with the expression vector thus obtained, and then the transformant is cultured in a proper medium, the secretory protein of the present invention can be secreted into the culture medium as the aimed polypeptide. Then, by linking to cDNA fragment coding other polypeptides, for example, common region (Fc portion) of antibody, fusion proteins can be produced. Polypeptides obtained by the method above can be isolated and purified by conventional biochemical methods.

INDUSTRIAL APPLICABILITY

The present inventors have confirmed that the polypeptide is more highly expressed in neointima than in tunica media of vascular smooth muscle. So it is suggested that the polypeptide of the present invention is useful for therapeutic treatment in restenosis after PTCA and arterial sclerosis in the field of cardiovascular system.

Further, since the polypeptide of the present invention showed the suppressive activity of cell proliferation in experiments and the structural similarity to that of VEGF, it is suggested that the polypeptide may possess the following activities.

(1) Cytokine activity and cell proliferation/differentiation activity

Since the polypeptide of the present invention suppresses cell proliferation in the over-expression system, it may exhibit cytokine activity, cell proliferation (either inducing or inhibiting) activity or cell differentiation (either inducing or inhibiting) activity or may induce or suppress production of other cytokines in certain cell populations (2) Immune stimulating/suppressing activity The polypeptide of the present invention may also exhibit immune stimulating or immune suppressing activity. The polypeptide of the invention may be useful in treatment of various immune deficiencies and disorders, for example, in regulating (stimulating or suppressing) growth and proliferation of T and/or B lymphocytes, as well as acting on the cytotoxicity of NK cells and other cell populations. Especially, it is suggested that the polypeptide of the present invention may exhibit suppressing activities against lymphogenous tumor metastasis induced by tumor vascularization.

(3) suppressing activity against ischemic vascularization

The polypeptide of the present invention may suppress diabetic retinopathy. It is known that VEGF exhibits activity of vascularization induced by ischemia. The vascularization in diabetic retinopathy is also ischemic vascularization after formation of avasocular regions of retina. Structural similarity to neurophilin suggest that the protein of the present invention may suppress growth of blood vessels as a novel VEGF receptor, therefore, may exhibit a therapeutic effect on diabetic retinopathy.

Administration or use of the protein or of CDNA coding the protein(for example, gene therapy(including regenerative therapy) or vectors suitable for cDNA transfection) may provide the effect or biological activities described about the protein of the invention.

Quantitative analysis of the polypeptide of the present invention in vivo can be performed using polyclonal or monoclonal antibodies against the polypeptide of the present invention. It can be used in studies on relationship between this polypeptide and disease, or diagnosis of disease, etc. The polyclonal and the monoclonal antibodies can be prepared using this polypeptide or its fragment as an antigen by conventional methods.

Identification, purification or molecular cloning of known or unknown proteins(ligands) which are connected with the polypeptide of the present invention can be performed using the polypeptide of the present invention by, for example, preparation of the affinity-column.

identification of molecules which interact with the polypeptide, molecular cloning of the gene may be conducted, for example, by western blot, using the polypeptide, or by yeast two-hybrid method, using the cDNA (desirably cDNA coding the polypeptide).

Screening method, which can identify agonists or antagonists against the polypeptide receptor and inhibitors against interaction between receptors and signal transduction molecules may be performed by using the polypeptide.

For example, the screening method could be performed by the following steps:

a) The polypeptide of the invention, compound to be screened and reaction mixture including cells are mixed (the reaction mixture includes peptides except markers which are transferred into cells as the cell grows and except the polypeptide for efficient observation of the function of the polypeptide.) under condition which the cells are normally stimulated by the polypeptide, then, b) it is determined whether the compound is a useful agonist or antagonist by measuring the cell growth.

The cDNA of the invention may be useful not only as an important and essential template in production of the polypeptide of the present invention which is expected to have a considerable utility, but also for diagnoses and treatments of hereditary diseases(treatments of gene deficiency or treatments which anti-sense DNA (RNA) s intercept expression of polypeptides, etc). In addition, genomic DNAs may be isolated by using cDNA of the invention as a probe.

Administration and dosing

To practice with diseases mentioned above, administration of the polypeptide of the invention or its antibodies can be carried out in general or local, generally peroral or parenteral ways. Oral, intravenous and intracerebroventricular administration are preferred.

The dosage to be administered depends upon age, body weight, symptom, desired therapeutic effect, route of administration, and duration of the treatment etc. In human adults, one dose per person is generally between 100 μg and 100 μg by oral administration up to several times per day, and between 10 μg and 100 μg by parenteral administration up to several times per day.

As mentioned above, the doses to be used depend upon various conditions. Therefore, there are cases in which doses lower than or greater than the ranges specified above may be used.

The polypeptide or the compounds of the present invention, may be administered as solid compositions, liquid compositions or other compositions for oral administration, as injections, liniments or suppositories etc. for parenteral administration.

Examples of solid compositions for oral administration include compressed tablets, pills, capsules, dispersible powders and granules. Examples of capsules include soft capsules and hard ones.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), stabilizing agents (such as human serum albumin, lactose etc.), and assisting agents for dissolving (such as arginine, asparaginic acid etc.).

The tablets or pills may, if desired, be coated with a film of gastric or enteric materials (such as sugar, gelatin, hydroxypropyl cellulose or hydroxypropylmethyl cellulose phthalate, etc.), or be coated with more than two films. And then, coating may include containment within capsules of absorbable materials such as gelatin.

Liquid compositions for oral administration may contain pharmaceutically-acceptable emulsions, solutions, suspensions, syrups and elixirs, and also may contain inert diluent(s) commonly used (purified water, ethanol etc.). Besides inert diluents, such compositions may also comprise adjuvants (such as wetting agents, suspending agents, etc.), sweetening agents, flavoring agents, perfuming agents, and preserving agents.

Other compositions for oral administration include spray compositions which may be prepared by known methods and which comprise one or more of the active compound(s) Spray compositions may comprise additional substances other than inert diluents: e.g. Stabilizing agents (sodium sulfite etc.), isotonic buffer (sodium chloride, sodium citrate, citric acid, etc.). For preparation of such spray compositions, for example, the method described in the U.S. Pat. No. 2,868,691 or 3,095,355 (herein incorporated in their entireties by reference) may be used.

Injections for parenteral administration include sterile aqueous or non-aqueous solutions, suspensions and emulsions. In such compositions, one or more active compound(s) is or are admixed with at least one inert aqueous diluent(s) (distilled water for injection, physiological salt solution, etc.) or inert non-aqueous diluents(s)(propylene glycol, polyethylene glycol, olive oil, ethanol, POLYSOLBATE 80 ™, etc.).

Injections may comprise additional compound other than inert diluents: e.g. preserving agents, wetting agents, emulsifying agents, dispersing agents, stabilizing agent (such as human serum albumin, lactose, etc.), and assisting agents such as assisting agents for dissolving (arginine, asparaginic acid, etc.).

DETAILED DESCRIPTION OF PREFERRED EMBODIMENTS

The invention are illustrated by the following examples, but not limit the invention.

EXAMPLE 1

Primary culture of normal human coronary artery endothelial cells (hCAEC) and smooth muscle cells (hCASMC) purchased from Clonetech and co-culture (an equal number of endothelial and smooth muscle cells were mixed and maintained in EGM-2-MV (trade name, a product of Bio Whittaker) for two days) were used as the sources for the construction of the cDNA libraries, and the yeast signal sequence trap (See U.S. Pat. No. 5,536,637) screening was carried out. ESDN containing CUB domain was isolated from cDNA library derived from the co-culture.

EXAMPLE 2

The cloning of 5'- and 3'-end regions of cDNA were performed by 5'- and 3'-RACE (Rapid Amplication cDNA End) methods using the Marathon cDNA Amplification Kit (trade name, a product of CLONTECH) to isolate the full-length cDNA. Mouse and rat counterparts were obtained with RT-PCR using two kinds of primer pairs based on human sequence data.

Mouse Primers:

5'-CTG-CTC-CAA-CTC-CTC-CTC-CTT-C-3'  (SEQ ID NO.10)

5'-CTG-CTT-CAT-TCC-TTT-CCA-CCA-ACC-TG-3'  (SEQ ID NO.11)

Rat Primers:

5'-TGT-GCT-GGT-CAT-GGT-CCT-CAC-TAC-TCT-C-3'  (SEQ ID NO.12)

5'-TGT-GCT-TTA-AAA-CGA-TGC-TTT-G-3'.  (SEQ ID NO.13)

As a result, it was revealed that alignment of human, mouse, and rat amino-acid sequences showed high homology between them. However, 5'-RACE method could not reach 5'-terminal sequence containing the definitive start codon, ATG,_in any species, resulting from high GC-content in the 5'-region of ESDN. Therefore, the inventors conducted mouse genomic library screening with Lambda FIXIT library (tradename, a product of Stratagene Inc.), to obtain two positive clones containing translation initiation site (Met). Human and rat counterparts were obtained with RT-PCR using a sense primer of 5'-GCA-CTA-TGC-GGG-CGG-ATT-GC-3' (SEQ ID NO. 14) containing the first methionine of mouse ESDN and an anti-sense primer of 5'-GGA-TGT-AAG-GGT-TCC-ACT-CTC-AGG-3' (SEQ ID NO. 15) situated in the downstream exon (which is not included in genomic clone). Alignment of three products are shown in FIG. 1 with amino-acid homology between human and rodents and between mouse and rat was 84-5% and 92%, respectively.

A motif search revealed that ESDN is a type-I transmembrane protein composed of a CUB domain and a factor FV/VIII-like domain and resembles neuropilin(with two CUB domains, two factor FV/VIII domain and a MAM domain) in the structure . A sequence homology search of the other area revealed that a region has significant homology with Limulus factor C and Coch, which is one of causal genes for deafness disorder, and has the conservative domain with four cysteines. In Coch domain, all four kinds of mutations identified to date in DFNA9 deafness disorder converge. Therefore, this domain has been detected in the protein of Limulus which was disassociated from genealogical tree in the evolution, so that it is suggested that the structure of this domain could be a novel domain structure.(Shown in FIGS. 2 and 3)

EXAMPLE 3

Human ESDN constructs were cloned into pEF6V5-His (tradename, a product of Invitrogen Corp.), swapping the original V5 epitope with the FLAG tag. These expression vectors were transfected into 293T and COS7 cells with Cell-Phect (trade name, a product of Amersham BioSciences) and Lipofectamine (tradename, a product of Life Technologies, Inc.), respectively. Further, after preparing cell lysate, the target protein was detected by western analysis using various antibodies.

Figure 6:
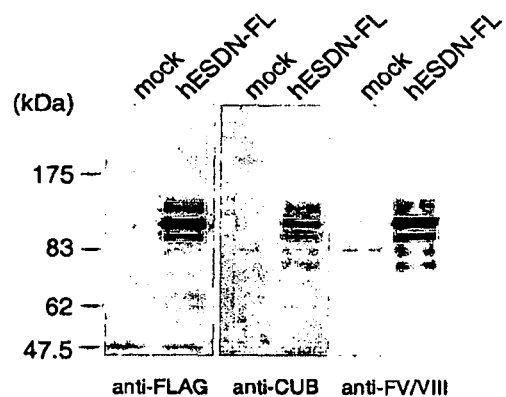
FIG. 6 shows Western blot analysis of the recombinant full-length ESDN.

Rabbit anti-CUB and anti-FV/VIII polyclonal antibodies were raised against KLH-conjugated polypeptides of GER-IRIKFGDGDIEDSD (SEQ ID NO. 16) and QDKIFQGNKDYHKDVRNN (SEQ ID NO. 17), respectively, and affinity-purified against each polypeptide by Sawady Technology. western analysis was carried out following the ECL (trade name, a product of Amersham BioSciences) or Renaissance (trade name, a product of NEN Life Science) western blot protocols. The other antibody used are anti-FLAG M2 monoclonal antibody (trade name, a product of Sigroa-Aldrich Co.). As a result, 127, 106, 93 Kda protein bands, which have not been detected in the lysate from cells transfected with expression vector only were detected. (Shown in FIG. 6)

EXAMPLE 4

Figure 7:
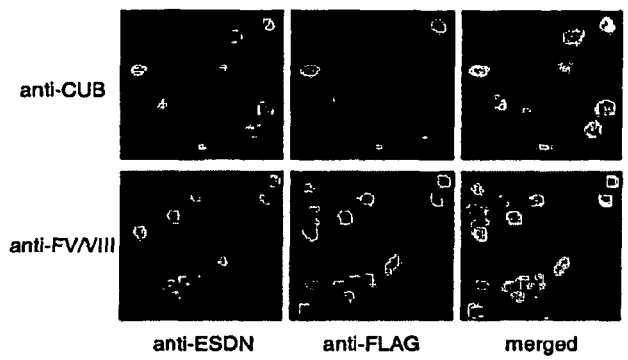
FIG. 7 shows images of surface expression of ESDN.

Hydrophobicity profile of ESDN amino acid sequence revealed that the predicted signal sequence of ESDN is very long and atypical. COS7 cells transfected with human full-length cDNA were fixed in 4% paraformaldehyde solution and reacted with the primary antibody for 30 minutes at room temperature, followed by reaction with the second antibody for 30 minutes. Then, they were observed and analyzed under a Bio-Rad confocal laser scanning microscope after double-staining with texas red anti-mouse IgG (trade name, a product of Vector Libraries, Ltd.) and FITC-anti-rabbit IgG (Jackson Laboratories). As a result, it was confirmed that this protein is expressed on the cell-surface. (Shown in FIG. 7)

Then, the inventors tried to confirm the location of a signal sequence cleavage site.

Figure 5:
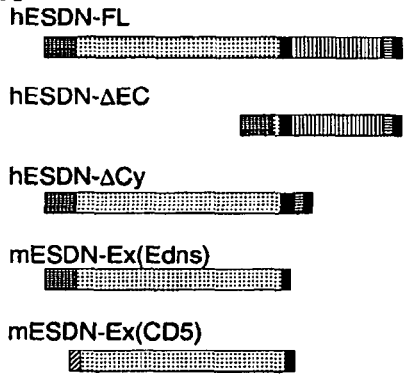
FIG. 5 shows a schematic view of the expression vectors.
Figure 8:
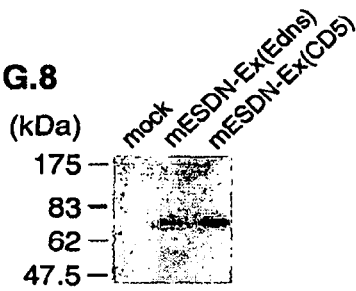
FIG. 8 shows Western blot analysis revealing that the longest secretory signal sequence of ESDN is cleavable at the predicted site.

Mouse ESDN constructs was re-cloned into an expression vector PCAGGS with mESDN-Ex(Edns), which was constructed with C-termini of the extracellular portion of mouse ESDN linked with 6xHis tag. Further, another construct, mESDN-Ex (CD5), whose signal sequence was replaced by that of human CD5; MPMGSLQPLATLYLLGMLVASVLA (SEQ ID NO. 18) was prepared. 293T cells were transiently transfected with these constructs, and culture media were analyzed by Western blot using the His-probe H-15 polyclonal antibody (trade name, a product of Santa Cruz Biotechnology Inc.) to detect the target proteins. As a result, it was confirmed that both constructs, mESDN-Ex(Edns) and mESDN-Ex (CD5) yielded the protein product of exactly the same size. (Shown in FIG. 5) As the size of human CD5 is shorter than that of mouse ESDN 39 amino-acid residues, this result supports that the two proteins belong to the same location of signal sequence cleavage sites. (Shown in FIG. 8)

EXAMPLE 5

Figure 9:
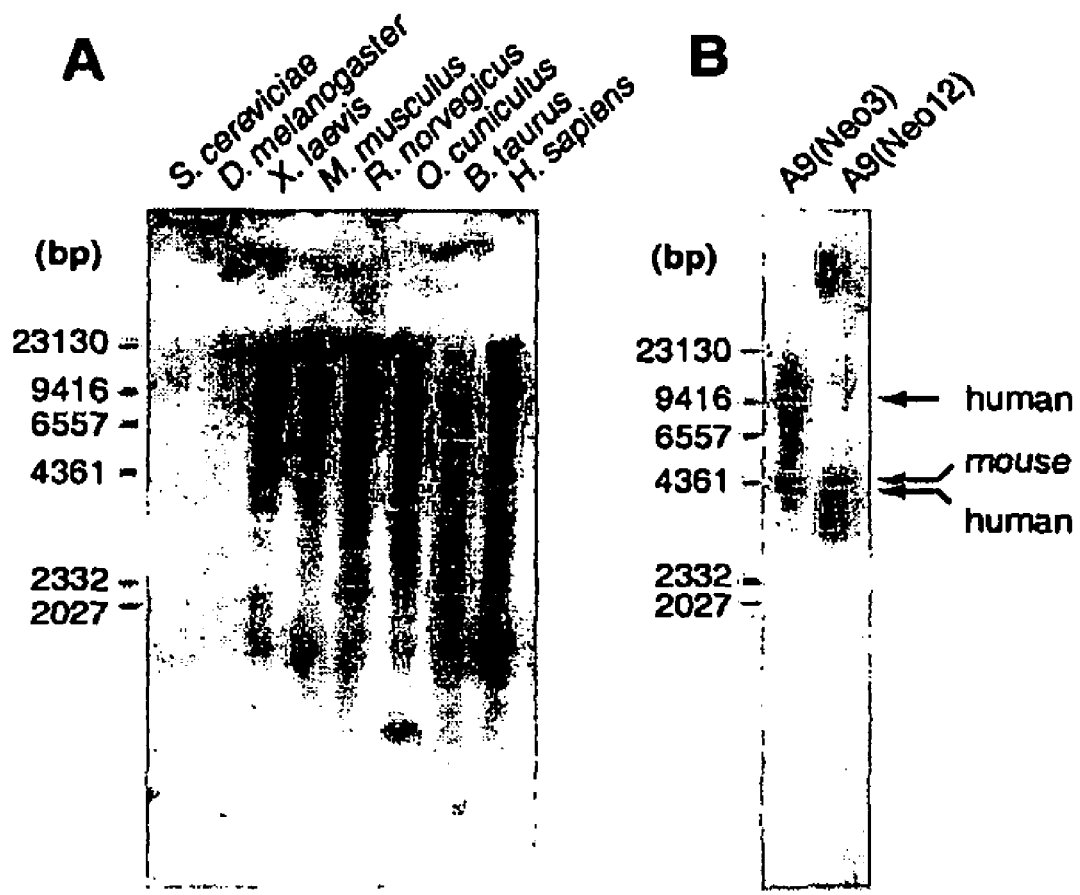
FIG. 9A shows Southern zooblot analysis of ESDN performed with human ESDN cDNA as a probe and 9B shows that human ESDN gene is on chromosome 3.

A Southern zooblot analysis was performed with a human ESDN probe labeled with [$^{32}$p]dCTP in all mammals (mouse, rat, rabbit, cow, and human), Xenopus, fly and yeast (at37° C., washing with 1xSSC). In addition to strong bands observed in all mammals, weak bands were detected in xenopus. No bands were observed in fly and yeast. (Shown in FIG. 9A)

EXAMPLE 6

Search for STS (sequence-tagged site)in human ESDN sequence revealed that it contains two independent STS clones, st SG29921 and sts-D29024, which are mapped at the neighborhood of D3S1603-D3S1271 and D3S1552-D3S1603 in radiation hybrid map (sites expected to correspond to chromosome 3q11.2 in cytegenetics map), respectively. To confirm this database result, mouse cell lines A9 (Neo3) and A9 (Neol2) (JCRB Cell Bank) were used for genomic southern hybridization. As human ESDN probe identified a cross-hybridized mouse band in both lanes, mouse ESDN was confirmed inboth A9 (Neo3) and A9 (Neol2), whereas human bands were present in the lane of A9(Neo3) only. Thus, these result revealed that human ESDN gene is located within the range which corresponds to cytogenetic region of chromosome 3p11.2 (Shown in FIG. 9B)

EXAMPLE 7

Figure 10:
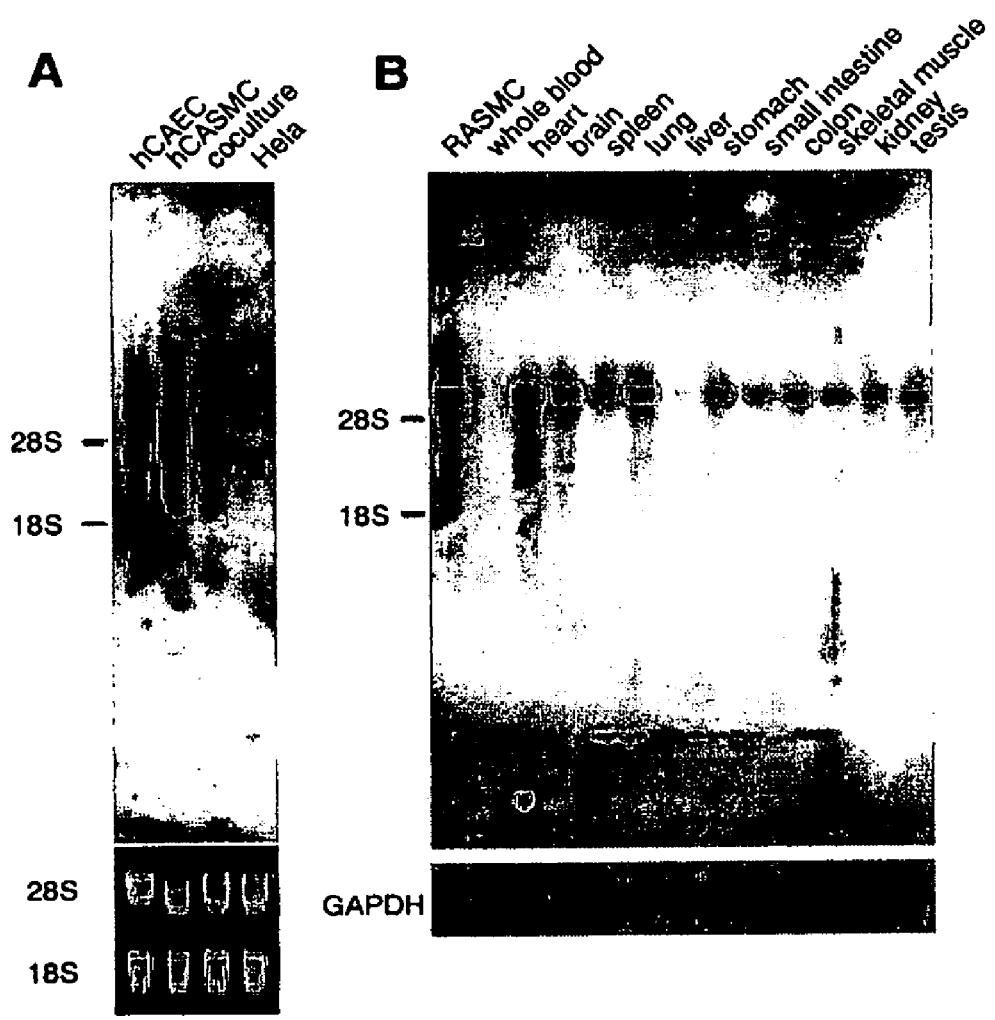
FIGS. 10A and B show Northern blot analysis with human cDNA and rat cDNA using RNA from human coronary arterial cells and rat organs or cultured aortic smooth muscle cells.

The total RNA prepared from hCAEC, hCASMC and the mixed co-culture using TRIzol(trade name, a product of Life Technologies) were used in Northern analysis of cultured human cells. In Northern analysis of rat organizations or cells, the total RNA prepared from the whole blood and other organizations or cultured cells using TRIzol LS and TRIzol respectively were used. Then, Poly (A)+RNA was purified with Oligotex™-dT30 Super (tradename, a product of Roche Molecular Biochemicals) and Northern analysis (at 65° C., washing with 0.2xSSC) was performed by using human and rat ESDN, their GAPDH probes labeled with [$^{32}$P]dCTP. ESDN was highly expressed in hCASMC(6.4, 3 kb), whereas the expression in hCAEC was weaker than in hCASMC. Further, no change of ESDN MRNA in the mixed co-culture was observed. (Shown in FIG. 10A)

In northern blot analysis for various rat cells or tissues, no ESDN was detected in whole blood cells, and the expression in liver was very faint. (Shown in FIG. 10B)

EXAMPLE 8 hCASMC was cultured in DMEM/2 mM glutanine depleted of serum for 48 hours, then was stimulated with the medium containing either of PDGF-BB, AT-II or FCS (tradenames, products of Sigma-Alsrich Co. and Life Technologies, Inc.) at the specified concentrations. Total RNA was extracted with TRIzol (trade name, a rpoduct of Life Technologies, Inc. ), cDNA was synthesized using Super Script Preamplification System for First Strand cDNA Synthesis Kit (Life Technologies, Inc.). Further, the mRNAs were measured by real-time quantitative RT-PCR using PE Applied Biosystems Prism Model 7700 Sequence Detection System. The nucleotide sequences of forward and reverse primers are as follows.

```
ESDN forward:
5'-CCC-AGC-AAG-GTG-ATG-GAT-G-3'         (SEQ ID NO.19)

ESDN reverse:
5'-CAA-GAA-TCA-GAA-TCT-TCA-ATG-TCA-     (SEQ ID NO.20)
AAG-3'

ESDN probe:
5'-(6-FAM)-CCT-GAG-AGT-GGA-ACC-CTT-     (SEQ ID NO.21)
ACA-TCC-ATA-AAC-(TAMRA)-3'
```

These were based on the human sequence, but were confirmed to be applicable in quantitative measurements of rodent transcripts as well. The nucleotide sequences of human GAPDH are as follows.

```
Human GAPDH forward:
5'-GAA-GGT-GAA-GGT-CGG-AGT-C-3'      (SEQ ID NO.22)

Human GAPDH reverse:
5'-GAA-GAT-GGT-GAT-GGG-ATT-TC-3'     (SEQ ID NO.23)

Human GAPDH probe:
5'-(VIC)-CAA-GCT-TCC-CGT-TCT-CAG-CC- (SEQ ID NO.24)
(TAMRA)-3'
```

Taq Man Rodent GAPDH Control Reagents (PE biosystems) were used for measurements of rat GAPDH. The mRNA level of ESDN and GAPDH means the number of copies, so standard curves could be prepared from known amount of plasmids with ESDN or GAPDH amplicon subcloned into pBlueScript SK(-) (Stratagene), and the ESDN mRNA level normalized to that of GAPDH was used for further analyses.

Figure 11:
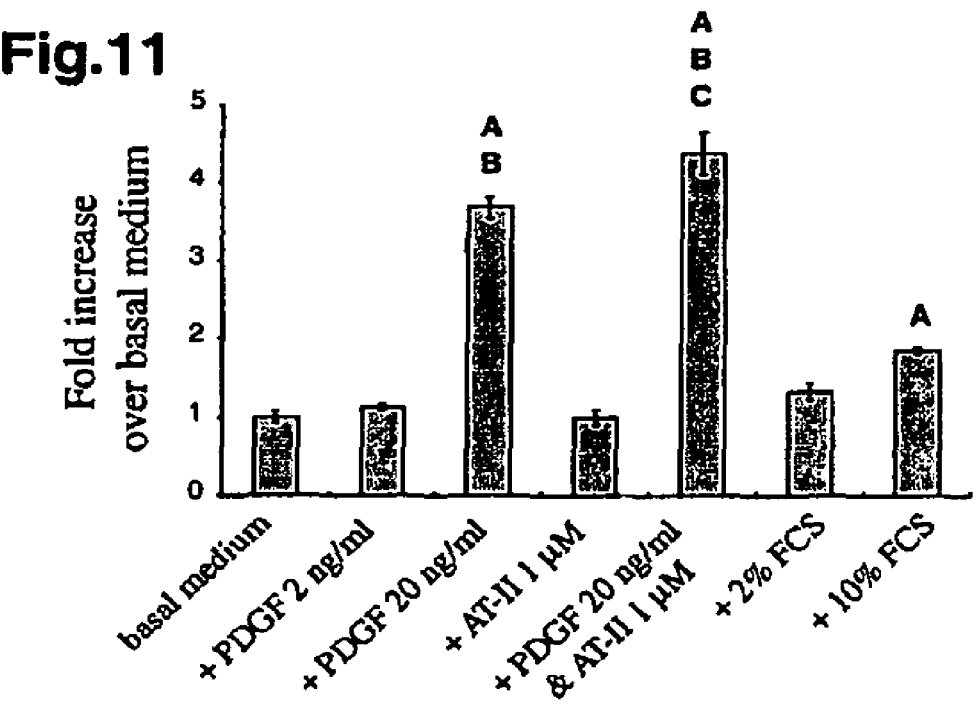
FIG. 11 shows an induction of ESDN mRNA in human coronary artery smooth muscle cells in response to PDGF-BB or FCS stimulation.

The results of quantitative RT-PCR showed that ESDN was up-regulated with PDGF-BB dose-dependently, but not with AT-II stimulation. FCS also up-regulated ESDN expression dose-dependently, but much less than PDGF-BB. (Shown in FIG. 11)

EXAMPLE 9

Figure 12:
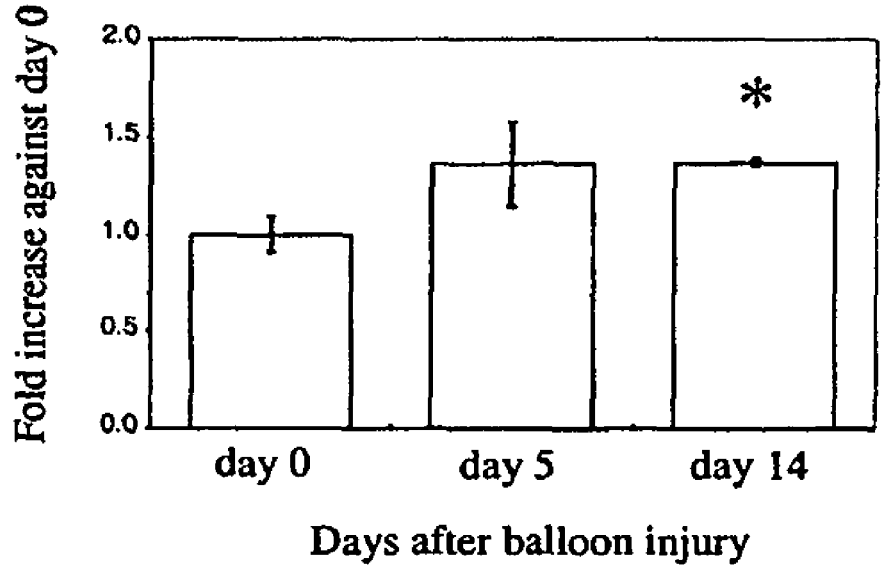
FIG. 12 shows up-regulation of ESDN mRNA in balloon-injured rat carotid arteries.
Figure 13:
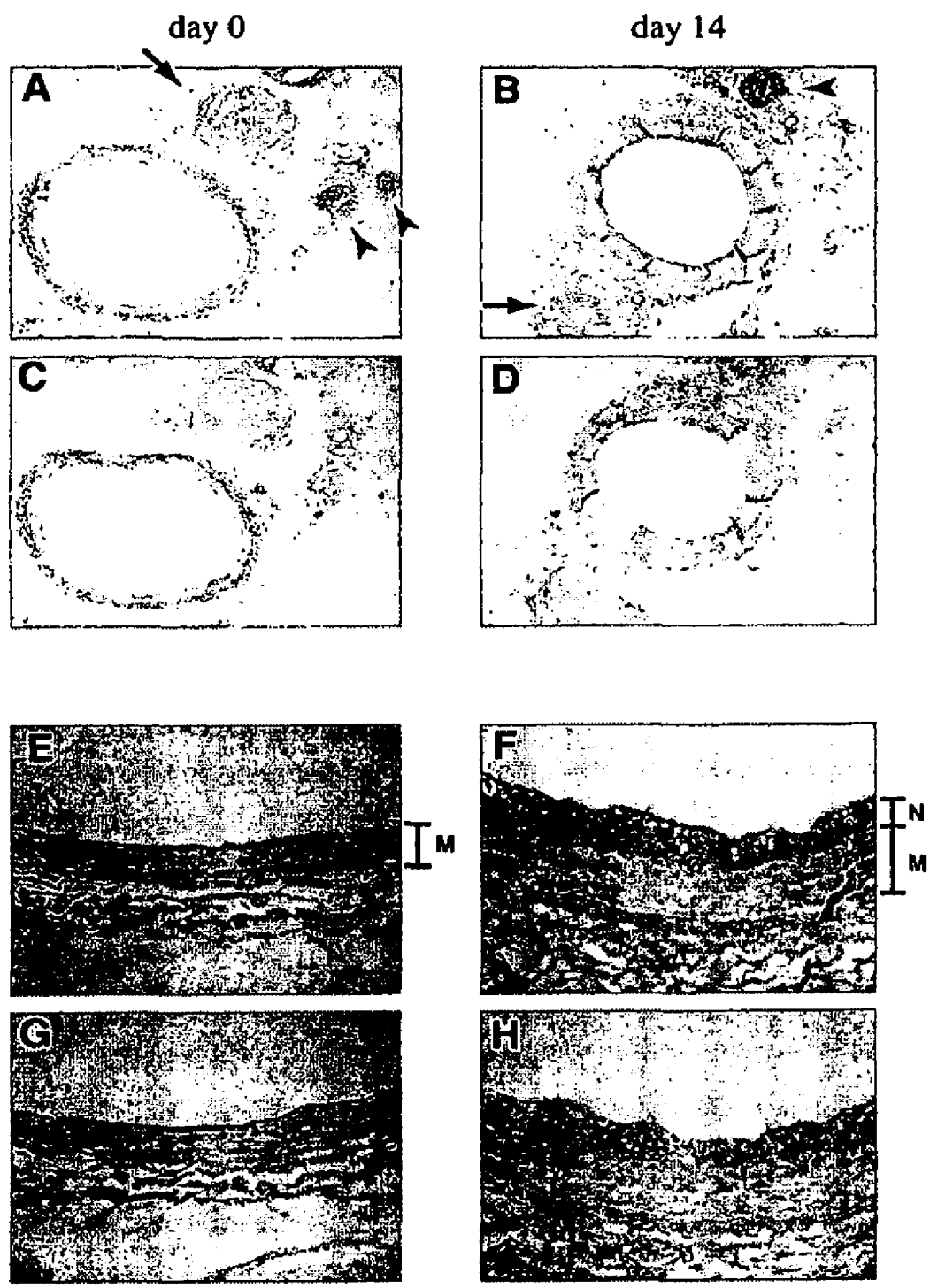
FIG. 13 shows immunohistochemical staining which reveals up-regulation of ESDN protein in the rat carotid artery after balloon injury.

The carotid arteries were harvested at 0, 5 or 14 days after balloon injury (n=5 on day 0, 5, n=4, on day 14). Total RNA was extracted with TRIzol (trade name, a product of Life Technologies, Inc.), cDNA was synthesized using Super Script Preamplification System for First Strand cDNA Synthesis Kit (Life Technologies, Inc.). Further, the mRNAs were measured by real-time quantitative RT-PCR using PE Applied Biosystems PrismModel 7700 Sequence Detection System. Quantitative RT-PCR analysis revealed that rat ESDN mRNA expression showed a tendency of up-regulation at day 5, and an significant increase at day 14 by 30%. Then, to elucidate the expression of ESDN, an immunohistochemical study was performed. (Shown in FIG. 12) Under anesthetization, treated or untreated rats were perfused with physiological saline cooled at 4° C. in advance. Then, the local perfused tissues were fixed with cold 4% paraformaldehyde, the harvested carotid arteries were embed in Tissue-Tek O.C.T. Compound(trade name, a product of Sakura Finetechnical Co., Ltd.) on dry-ice/ethanol bath. The embeded carotid arteries were sliced in the thickness of 4 μm and were immunohistochemistrically analyzed by the method using avidin-biotin-alkaline phosphatase complex (Vector Laboratories). The substrate, Vector Red(tradename, a product of Vector Laboratories, Inc.), which reacted with alkaline phosphatase stained the slices, to contrast with methyl-green staining. As primary antibodies, rabbit anti-peptide polyclonal antibodies were used at the concentration of 5-10 μg/ml, and normal rabbit IgG (DAKO) were used at the same concentration for negative controls. The result revealed that tunica media of aorta and common carotid arterie in vascular smooth muscle were stained, and that parts (arrow) of central nervous system, brain and spinal cord, etc and peripheral part, vagus nerves (arrowheads), etc were rather conspicuously stained. (Shown in FIG. 13) A, B, E and F were stained by anti-CUB antibody, and C, D, G and H were stained by an equal concentration of rabbit IgG as a primary antibody (control). M and N shown in E and F indicate tunica media and neointima, respectively.

EXAMPLE 10

Figure 14:
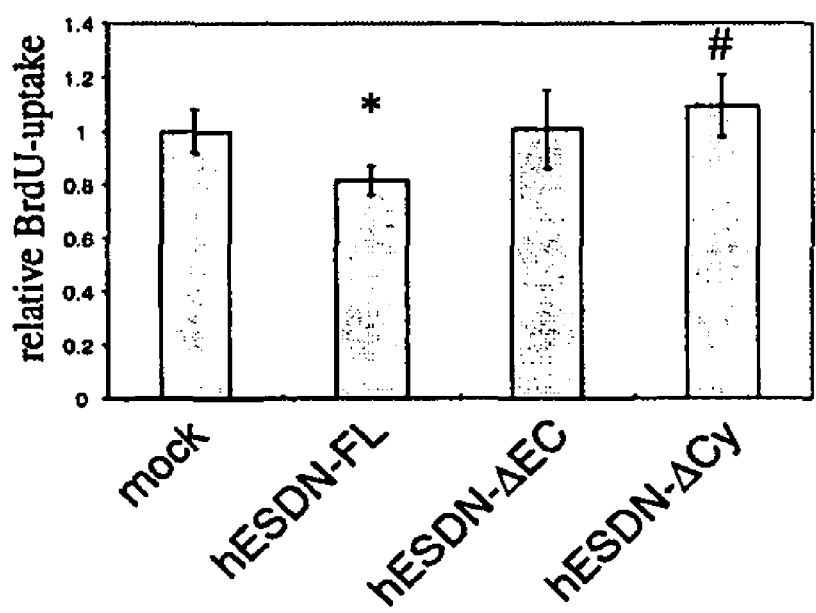
FIG. 14 shows suppression of BrdU uptake in cells overexpressing ESDN.

ESDN constructs of human full-length ESDN(hESDN-FL) and the deletion mutants (hESDN-ΔEC, hESDN-ΔCy) cloned into one expression vector were prepared with QIAfilter Plasmid Midi Kit(QIAGEN). Then, they were purified twice by phenol/CIAA extraction and once by CIAA extraction. 293T cells were transfected by these expression vectors using Cell Phect (Amersham Life Science). After 12 hours of incubation with transfection solution, the medium was replaced by fresh DMEM+10% FCS and incubated for 2 hours. Cells were collected using trypsin and replated in 96-well plates in duplicate. For one plate, 2-hour-BrdU pulse was applied after 24hours of culturing, and the incorporated BrdU was measured by Cell Proliferation ELISA, BrdU (calorimetric) (trade name, a product of Roche Diagnostics) The other plate was used to estimate the number of cells using Premix WST-1 assay kit (trade name, a product of TaKaRa Shuzo Co.) 2 hours after replating. (Shown in FIG. 14) The results revealed that uptaking of BrdU was significantly suppressed in cells with ESDN expressed therein, while such suppressing effects is weaker in cells without extracellular domains, and no such effects were observed in cells without intracellular domains.

What is claimed:

1. A cDNA encoding a polypeptide comprising the amino acid sequence of SEQ ID NO: 2, or encoding a polypeptide with ESDN function which comprises an amino acid sequence at least 95% identical to the amino acid sequence of SEQ ID NO: 2.

2. The cDNA according to claim 1, wherein said cDNA comprises the nucleotide sequence of SEQ ID NO: 3.

3. A replication or expression vector comprising the cDNA of any one of claims 1 or 2.

4. A host cell transformed with the replication or expression vector according to claim 3.

5. A method for producing a polypeptide comprising the amino acid sequence of SEQ ID NO: 2, or a polypeptide with ESDN function which comprises an amino acid sequence at least 95% identical to the amino acid sequence of SEQ ID NO: 2, wherein said method comprises culturing the host cell according to claim 4 under conditions effective to express the polypeptide.

* * * * *